(12) United States Patent
Arthur et al.

(10) Patent No.: US 8,232,229 B2
(45) Date of Patent: Jul. 31, 2012

(54) SEED TREATMENT FORMULATIONS AND METHODS OF USE

(75) Inventors: Karen S. Arthur, Plano, TX (US); Frank Gonzales, Walnut Creek, CA (US); Michael Seitz, Dublin, CA (US)

(73) Assignee: Valent U.S.A., Corporation, Walnut Creek, CA (US)

( * ) Notice: Subject to any disclaimer, the term of this patent is extended or adjusted under 35 U.S.C. 154(b) by 146 days.

(21) Appl. No.: 12/326,309

(22) Filed: Dec. 2, 2008

(65) Prior Publication Data

US 2009/0143447 A1 Jun. 4, 2009

Related U.S. Application Data

(60) Provisional application No. 60/991,969, filed on Dec. 3, 2007, provisional application No. 60/991,976, filed on Dec. 3, 2007, provisional application No. 60/991,985, filed on Dec. 3, 2007.

(51) Int. Cl.
*A01N 59/04* (2006.01)
(52) U.S. Cl. .................................................. 504/101
(58) Field of Classification Search ............... 504/101
See application file for complete search history.

(56) References Cited

U.S. PATENT DOCUMENTS

| 4,981,758 | A | 1/1991 | Chu et al. | |
|---|---|---|---|---|
| 2004/0118040 | A1* | 6/2004 | Asrar et al. | 47/57.6 |
| 2005/0107498 | A1* | 5/2005 | Kolter et al. | 524/35 |
| 2005/0124492 | A1* | 6/2005 | Asrar et al. | 504/100 |
| 2005/0159063 | A1 | 7/2005 | Hill et al. | |
| 2005/0191390 | A1* | 9/2005 | Krochta et al. | 426/302 |
| 2006/0240983 | A1 | 10/2006 | Yamaguchi | |
| 2007/0275101 | A1 | 11/2007 | Lu et al. | |
| 2007/0275985 | A1 | 11/2007 | Gebauer et al. | |
| 2011/0166022 | A1 | 7/2011 | Israels et al. | |

FOREIGN PATENT DOCUMENTS

| WO | WO 2005/048707 A1 | 6/2005 |
|---|---|---|
| WO | WO 2005048707 A1 * | 6/2005 |

OTHER PUBLICATIONS

Sigma Catalog, 2002-2003, p. 1731.*

* cited by examiner

*Primary Examiner* — Johann Richter
*Assistant Examiner* — Thor Nielsen
(74) *Attorney, Agent, or Firm* — Wood, Phillips, Katz, Clark & Mortimer

(57) ABSTRACT

The present invention generally relates to aqueous seed treatment formulations comprising a pesticidal agent, a polyvinyl alcohol (PVA), a graft copolymer, and a plasticizer. In one embodiment of the invention, PVA-compatible polymer emulsions are employed. The present invention also relates to uses of the disclosed compositions for protecting seeds from pests.

32 Claims, No Drawings

SEED TREATMENT FORMULATIONS AND METHODS OF USE

FIELD OF THE INVENTION

The present invention generally relates to aqueous seed treatment formulations that protect plant propagation material against attack by pests and their methods of use.

BACKGROUND OF THE INVENTION

The practice of treating seeds or other plant propagation material with pesticide formulations is well known. Insecticides and fungicides are applied to seeds to protect them from pests through the early stages of plant development in the soil. Two types of pesticide formulations are typically used: wettable powders and aqueous flowables.

Commercial seed treatments require specialized equipment to properly apply treatments or to treat large volumes of seed. The seed treatment equipment (a seed treater) combines commercially available formulations to make slurries of pesticides. Examples of seed treaters include Gustafson Accu-Treat® RH-24, Accu-Coat® HC 3000, and the like. A commercial pesticide formulation is usually formulated as a suspension concentrate. A seed treater is also used to add stickers, binders, polymers, and/or colorants to the pesticide slurry to improve handling and safety. The additives reduce dusting, and the colorants alert agricultural workers to the chemical treatment.

The number of additives and the amount of pesticide per seed that can be used in seed applications are limited by the coating and drying techniques available with commercial seed treating equipment. Each crop can adsorb just a limited amount of fluid, beyond which the seeds cannot be properly dried and/or handled in the seed processing equipment or planting equipment.

Furthermore, many existing formulations contain high concentrations of low molecular weight (LMW) surfactants. These LMW surfactants are typically added to stabilize the dispersion of the pesticide and to provide a stable pumpable suspension for ease of use by the treater. One of the problems associated with LMW surfactants is that they are known to increase the stress on seeds and can reduce germination.

Another problem with using ad hoc mixtures of pesticides, polymers, colorants, and other additives is the need for multiple applications to deposit and dry the desired amounts of pesticides and additives on the seeds. Multiple applications are necessary for proper adhesion.

In addition to being time consuming, the safety of these application mixtures is often unknown and problematic. Often, fillers, such as talc, are needed to reduce phytotoxicity or to improve seed drying and handling properties. As a result, handling is rendered difficult and the biological efficacy of the seed treatment is reduced.

Therefore, there is a need in the art for an effective non-phytotoxic all-inclusive formulation that adheres pesticides to seeds and eliminates the need to add further binders or polymers to the application mixture by a seed treater. Ideally, such a formulation can be processed in continuous flow in a single-pass application without fillers or anti-blocking powders.

SUMMARY OF THE INVENTION

All percents by weight and ratios for the components in the descriptions of the compositions of the invention are for 100% active material, unless otherwise specified.

The present invention provides an aqueous formulation comprising a) at least one pesticidal agent; b) polyvinyl alcohol (PVA); c) a graft copolymer; and d) a plasticizer. The pesticidal agent may be either an insecticide or a fungicide. More specifically, the plasticizer usually comprises a blend of liquid and solid plasticizers.

In one embodiment, the plasticizer is water-miscible. It may also comprise a glycol or a polyol.

In a preferred embodiment, the ratio of the liquid plasticizer to the solid plasticizer is from about 3-to-1 to about 1-to-3 with the most preferred ratio from 1.5-to-1 to about 1-to-1.5 parts by weight.

In another embodiment, the formulation further comprises a PVA-compatible polymer emulsion. The polymer emulsion may be based on an ethylene vinyl acetate copolymer.

In another embodiment, the graft copolymer is comb-branched.

In another embodiment, the formulation comprises no more than about 0.25% by weight of the total formulation of a low molecular weight (LMW) surfactant.

In another embodiment, the invention provides a method for treating seeds comprising applying a composition of the present invention to seeds to be treated.

In a preferred embodiment, the formulation comprises from about 20% to about 50% by weight of the total formulation of a pesticidal agent; from about 1.0% to about 3.0% by weight of the total formulation of a PVA-graft copolymer combination where the PVA to graft copolymer ratio is from about 10-to-1 to about 1-to-2 parts by weight; and the amount of plasticizer is from about 5.0% to about 15.0% by weight of the total formulation.

In a more preferred embodiment, the formulation comprises from about 35% to about 50% by weight of the total formulation of a pesticidal agent; from about 1.0% to about 3.0% by weight of the total formulation of a PVA-graft copolymer combination where the PVA to graft copolymer ratio is from about 5-to-1 to about 1.5-to-1 parts by weight; and from about 7.0% to about 12.0% by weight plasticizer of the total formulation.

In the most preferred embodiment, a formulation comprises about 0.07-0.25% by weight of the total formulation of a thickener; about 1.1-1.4% by weight of the total formulation of PVA; about 3.5-4.4% by weight of the total formulation of propylene glycol or glycerol; about 3.5-4.4% by weight of total formulation of sorbitol; about 0.2-0.4% by weight of the total formulation of a graft copolymer; about 0.1% by weight of the total formulation of a wetting agent; about 0.03-0.1% by weight of the total formulation of a defoamer; about 0 to 0.1% by weight of the total formulation of a preservative and either (1) about 48.0% by weight of the total formulation of clothianidin, or (2) about 40% by weight of total formulation of ethaboxam or metconazole; the balance of the formulation is water to total 100% by weight.

In another preferred embodiment, the formulation further comprises about 0.07% organic thickener by weight of total formulation, no inorganic thickener, and about 3% of a wax slip agent emulsion or dispersion (weight percent is material "as supplied", usually about 20 to 55% solids in water).

In another preferred embodiment, the formulation further comprises about 3.0% by weight of the total formulation of a polymer emulsion (weight percent is material "as supplied", usually about 30 to 60% solids in water).

In another embodiment, the formulation further comprises about 0.1% of the total formulation of a wetting agent. In a preferred embodiment, the wetting agent is an LMW surfactant.

In another embodiment, the formulation further comprises from about 0.1% to about 1.0% by weight of the total formulation of additional formulation modifiers.

In a preferred embodiment, the PVA has an average molecular weight from about 12,500 g/mole to about 125,000 g/mole.

In another embodiment, the invention relates to a method of protecting seeds from pests comprising applying to seeds an effective amount of the claimed formulations.

In another embodiment, the invention relates to a method of protecting seeds from pests comprising applying to seeds an effective amount of the claimed formulations, wherein the polyvinyl alcohol (PVA) and the graft copolymer provide a protective layer between the pesticidal agents and the seeds. The protective layer prolongs seed shelf life.

In a preferred embodiment, the protective layer forms a membrane.

In yet another embodiment, the plasticizer is used to control the drying rate of the formulation.

The disclosed embodiments are simply exemplary embodiments of the inventive concepts disclosed herein and should not be considered as limiting, unless so stated.

DETAILED DESCRIPTION OF THE INVENTION

The present invention generally relates to formulations comprising a) at least one pesticidal agent; b) polyvinyl alcohol (PVA); c) a graft copolymer; and d) a plasticizer.

Applicants have discovered that graft copolymers work synergistically with polyvinyl alcohol (PVA) to produce a highly loaded suspension concentrate of insecticide(s) and/or fungicide(s) characterized by low viscosity and excellent stability. The synergy is important, since neither PVA alone nor graft copolymers alone can produce highly loaded suspensions of comparable viscosity or stability.

The terms "plant propagation material" and "seeds" are used interchangeably throughout the specification.

Formulations of the present invention can be used to prepare suspension concentrates of insecticides, fungicides, and their mixtures. Disclosed formulations can be used "as is", or mixed with other additives, or diluted with water. They may be applied to seeds either by themselves or simultaneously with other pesticides or additives.

Formulations of the present invention are non-phytotoxic.

At this point, various components of the disclosed formulations will be discussed in more detail.

Pesticidal Agents

Pesticidal agents that can be used in accordance with this invention are chemically stable in water at a pH within the range of 4 to 7 or 7 to 9, and preferably over the pH range of 4 to 9. They have low water solubility: normally, below 5000 parts per million (ppm) and preferably below 700 ppm at 20° C. In a preferred embodiment, the pesticidal agents are solids with melting points above 80° C., and in a more preferred embodiment, their melting points are above 100° C.

Pesticidal agents that can be used in accordance with this invention include insecticides; including but not limited to neonicotinoid insecticides like clothianidin, imidacloprid, thiamethoxam, acetamiprid, and thiacloprid; antibiotic insecticides like abamectin, emamectin benzoate, and spinosyns A and B; carbamate insecticides like bendiocarb, carbaryl, carbofuran, pirimicarb, isoprocarb, methiocarb, thiodicarb; pyrethroid insecticides like acrinathrin, deltamethrin; phenylpyrazole insecticides like ethiprole, fipronil; organochlorine insecticides like endosulfan; organophosphorus insecticides like coumaphos; diamide insecticides like chlorantraniliprole, flubendiamide; benzoylurea insecticides like bistrifluoron, chlofluazuron, diflubenzuron, flucycloxuron, hexaflumuron, novaluron, teflubenzuron, triflumuron; insect growth regulators like buprofezin; and similar classes of insecticides.

Pesticidal agents that can be used in accordance with this invention include fungicides, including but not limited to antibiotic fungicides like antimycin A1; stobilurin fungicides like azoxystrobin, dimoxystrobin, fluoxastrobin, kresoximmethyl; carbamate fungicides like benthiavalicarb-isopropyl, carbendazim, diethofencarb, iprovalicarb, thiophanate-methyl; dicarboximide fungicides like captafol, captan, famoxadone, folpet, iprodione, procymidone, vinclozolin; triazole fungicides like bitertanol, bromuconazole, cyproconazole, diclobutrazol, difenoconazole diniconazole epoxiaconazole, fenbuconazole, fluquinconazole, flutriafol, hexaconazole, imibenconazole, ipconazole, metconazole, prothioconazole, simeconazole, tebuconazole, triadimefon, triadimenol, triticonazole; amide fungicides like boscalid, carboxin, carpropamid, dicyclomet, ethaboxam, fenfuram, fenhexamid, flusulfamide, flutolanil, furametpyr, mepronil, ofurace, oxadixyl, pyracarbolid, thifluzamide, tiadinil, zoxamide; aromatic fungicides like chloroneb, chlorothalonil; imidazole fungicides like cyazofamid, fenamidone, triazoxide; the aliphatic nitrogen fungicides like cymoxanil; morpholine fungicides like dimethomorph; pyrimidine fungicides like fenarimol ferimzone, mepanipyrim, nuarimol, pyrimethanil; pyrrole fungicides like fenpiclonil, fludioxonil; pyridine fungicides like fluazinam, fluopicolide; benzimidazole fungicides like fuberidazole, thiabendazole; dithiocarbamate fungicides like mancozeb, maneb, thiram, ziram; quinoline fungicides like quinoxyfen; aromatic fungicides like quitozene; miscellaneous (unclassified) fungicides like diclomezine, dithianon, pencycuron, pyroquilon, tricylazole; 2-[2-(2,5-dimethylphenoxymethyl)phenyl]-2-methoxy-N-methylacetamide; and related types of fungicides.

The terms "insecticides" and "fungicides" are used broadly and are intended to cover all compounds active against insects and fungi. The compounds may belong to a wide range of compound classes. The pesticidal agents used in a formulation made in accordance with this invention may be a combination of the insecticides and fungicides selected to control a number of pests, insects and/or fungi, through the use of one formulation. Furthermore, it is anticipated that a formulation made in accordance with this invention may also contain auxiliary pesticidal agents that do not conform to the requirements set forth in this invention, provided that these auxiliary pesticidal agents are compatible with said formulation as determined by compatibility tests well known by those familiar with the art. For example, water-soluble pesticidal agents may be dissolved in the water carrier used in the formulation without affecting the suspension of the primary, solid pesticidal agents that are the subject of this invention. Another example of an auxiliary pesticidal agent is an encapsulated pesticidal agent, wherein a water-insoluble liquid or low melting insecticide and/or fungicide is enveloped by a solid shell or encased in a solid matrix, and then added to a formulation described in this invention.

Mixtures of insecticides and fungicides may also be utilized in the present invention. Mixtures are influenced by numerous factors such as the crop, geographic area, pest spectrum and pressure, and the prevalence of pesticide resistance. Fungicides mixtures usually contain at least one broad-spectrum fungicide that provides some control over many types of fungi that may be present. Triazole fungicides like metconazole and organophosphate fungicides like tolclofosmethyl are examples of broad-spectrum fungicides. A fungicide mixture is also likely to contain an oomycete-active fungicide. The Oomycetes, also known as water molds, resemble fungi and historically are still classified with fungi. The amide fungicides like metalaxyl and ethaboxam are examples of fungicides with oomycete-activity. Other fungicides may also be added to boost the control of specific fungi that plague a specific crop or provide a different mode of action. This is useful in managing fungicide resistance which is a major concern. The use of premixes of fungicides that control the same pest with different modes of action can prevent the development of resistance. Flutolanil is an example of a new fungicide used to improve control of Rhizoctonia fungi, and provides a different mode of action than the traditional strobilurin fungicides. Neonicotinoids have proven themselves to be highly effective, systemic insecticides for seed treatments. Presently preferred pesticides in mixtures are neonicotinoid insecticides such as clothianidin; triazole fungicides such as metconazole; and amide fungicides such as ethaboxam.

Representative such mixtures include:
clothianidin/metconazole;
Neonicotinoids/ethaboxam;
Neonicotinoids/2-[2-(2,5-dimethylphenoxymethyl)phenyl]-2-methoxy-N-methylacetamide;
Neonicotinoids/tolclofos-methyl;
metconazole/ethaboxam;
metconazole/2-[2-(2,5-dimethylphenoxymethyl)phenyl]-2-methoxy-N-methylacetamide;
ethaboxam/2-[2-(2,5-dimethylphenoxymethyl)phenyl]-2-methoxy-N-methylacetamide;
ethaboxam/tolclofos-methyl;
2-[2-(2,5-dimethylphenoxymethyl)phenyl]-2-methoxy-N-methylacetamide/tolclofos-methyl;
2-[2-(2,5-dimethylphenoxymethyl)phenyl]-2-methoxy-N-methylacetamide/metalaxyl;
2-[2-(2,5-dimethylphenoxymethyl)phenyl]-2-methoxy-N-methylacetamide/mefenoxam; and
2-[2-(2,5-dimethylphenoxymethyl)phenyl]-2-methoxy-N-methylacetamide/ipconazole.

Polyvinyl Alcohol (PVA)

Polyvinyl alcohol (PVA) is a water-soluble synthetic polymer. Many different grades of PVA are commercially available. While most of the available PVA polymers can be used in this invention, the preferred PVA grades have "Ultra Low", "Low" and "Medium" viscosity grades. They are usually classified by the viscosity of 4% PVA solutions. The viscosity of these PVA grades is generally between about 2.5 cP (centipoise) to about 32 cP at 20° C. The most preferred grades are the "Ultra Low" and "Low" viscosity grades.

The PVAs encompassed by the present invention have weight average molecular weights from about 12,500 g/mole to about 125,000 g/mole. Each grade of polymer has a distribution of molecular weights. The weight average molecular weight is defined as the molecular weight multiplied by the weight fraction of molecules that have that weight, summed over all the weights in the distribution, divided by the total weight. Further, the PVA polymers can be fully (98-100%), intermediately (90-98%), or partially (70-90%) hydrolyzed. Partially hydrolyzed PVA polymers are most preferred. Modified or special grades of PVA polymers can also be used. PVAs in the viscosity range disclosed above can be carboxylated or sulfonated to introduce some anionic properties that improve viscosity and dispersing power. These grades of PVA simply have some carboxylic groups ($-CO_2X$ group) or sulfonic groups ($-SO_3X$ group) added to the PVA chain, where X can be H or an alkali metal.

Examples of suitable PVAs include but are not limited to Celvol® 203 (trademark of Celanese Ltd.), Celvol® 205, Celvol® 502, Celvol® 513, Celvol® 518, Celvol® 523, Celvol® 103, Celvol® 305, Celvol® 310, Celvol® 325, Celvol® 418, Celvol® 425, and Erkol V 03/240, available from Celanese Ltd. Examples of special grades of PVA are the Gohsenal (carboxylated) and the Gohseran (sulfonated) products from Nippon Gohsei (The Nippon Synthetic Chemical Industry Co., Ltd).

Graft Copolymers

A graft copolymer is a material that has polymer chains of one chemical composition branching out from a polymer backbone with a different chemical composition. Graft copolymers that can be used in accordance with this invention include but are not limited to acrylic acid, methacrylic acid, acrylate, methacrylate or methyl methacrylate polymers which have chains of another polymer, as for example, a polyether such as polyethylene glycol, extending from the acrylate polymer backbone.

In a preferred embodiment, the graft copolymers are comb-branched polymers with an acrylic acid, methacrylic acid, acrylate, methacrylate or methyl methacrylate polymer backbone and hydrophilic polyethylene glycol (PEG) branches extending from this backbone. In two-dimensional representations, the PEG branches are drawn perpendicular to the acrylate polymer backbone (usually linear) and resemble the teeth of a comb, giving rise to the description "comb-branched". The comb-branched graft copolymers used in the present invention are proprietary materials; therefore, specific details of their composition and manufacture are not known to the applicants.

Suitable comb-branched graft copolymers include, but are not limited to Tersperse® 2500 (about a 35% graft copolymer solution from Huntsman Corp.), Atlox® 4913 (about a 35% graft copolymer from Croda Uniqema.), Ethacryl P® (a 35-45% graft copolymer solution from Lyondell Chemical Co.), and the like.

PVA-Graft Copolymer Combinations

The synergistic PVA and graft copolymer combination is a mixture of these two polymers, wherein the relative proportions of PVA and graft copolymer are from a ratio of about 10-to-1 (PVA-to-graft copolymer) to a ratio of about 1-to-2 (PVA-to-graft copolymer) parts by weight.

In a preferred embodiment, the ratio of PVA to graft copolymer is from about 5-to-1 to about 1.5-to-1 parts by weight.

In preferred formulations of the present invention, the total concentration of the polymer combination is from about 1.0% to about 3.0% by weight of the total formulation.

There are many advantages to using the PVA-graft copolymer combination.

First, the polymer combination coats the pesticidal agent used in the formulation and provides a protective layer between the pesticidal agent and the seed. This protective layer reduces any phytotoxicity that the pesticidal agent may have.

Second, the polymer combination eliminates the need for any significant concentration of low molecular weight (LMW) surfactants. In this context, by the term "significant", applicants mean a concentration higher than about 0.25% by weight of LMW surfactant in the formulation. LMW surfactants, particularly non-ionic surfactants, are known to disrupt protective lipophilic layers regulating moisture uptake that surround the seed. The disruption of these lipophilic layers permits very rapid moisture intake upon planting, which can result in a decrease in germination. High molecular weight, water-soluble polymeric dispersants disclosed in this application are less likely to degrade these protective layers. Further, many LMW surfactants are inherently phytotoxic.

Accordingly, the formulations of this invention require only trace amounts of LMW surfactants, for purposes of film wetting and coverage on the seed. Typically, only about 0.1% or less by weight of LMW surfactant is needed to achieve good wetting in a formulation comprising up to 50% of pesticidal agent. For comparison purposes, prior art suspension concentrates typically require from 1% to 20% by weight of LMW surfactants.

Third, water-soluble polymeric materials used in formulations of the invention provide for slower uptake and translocation of the pesticidal agent into the seeds. In prior art formulations, LMW surfactants are often used to enhance the uptake and the translocation of pesticidal agents into the seeds. However, quick uptake can exacerbate any toxicity that the surfactant or the pesticidal agent may possess, resulting in a decrease in germination.

Another advantage of the formulations of this invention is that they improve the adhesion of the pesticidal agent to the seeds. The PVA-graft copolymer combination is a good film former with high binding capacity. In many applications, this quality alone is sufficient to secure the pesticidal agent on the seeds and to prevent it "dusting off" during typical seed handling. Therefore, there is no need for polymer additions by the seed treater.

In addition, the PVA-graft copolymer combination is very water-soluble and safe on seeds. Seeds coated with the film formed by the formulations of the present invention can easily be re-hydrated by soil moisture. The film does not function as a limiting factor in the transport of moisture into seeds. The seeds' normal lipophilic layers are preserved and remain the controlling factor in moisture uptake by the seeds. Accordingly, good seed germination and coating adhesion are maintained.

Furthermore, the PVA-graft copolymer combination is compatible with dispersant systems employed in many commercial polymer emulsions. This compatibility permits the incorporation of polymer emulsions directly into the seed treatment formulation at the point of manufacture without loss in stability.

Plasticizers

Plasticizers that can be used in formulations of the present invention preferably comprise a blend of liquid plasticizers and solid plasticizers. As used herein the term "plasticizer" refers to a substance that is used to modify the film produced by the formulations, to allow faster drying, and to impart greater moisture sensitivity without the need for tack that can impair the flow of the seed in handling and planting equipment.

The plasticizer modifies the physical properties of the polymer film deposited on a surface. Tack and adhesion strength are the properties of particular interest. The liquid plasticizer's effect on the film is normally opposite to that imparted by the solid plasticizer. The liquid plasticizer normally increases tack, and the solid plasticizer normally decreases it. A blend of liquid and solid plasticizers can then be used to mitigate or cancel the effects of an individual plasticizer, thereby allowing much higher concentrations of a liquid-solid plasticizer blend to be used in comparison to (say) just a liquid one. In this manner, the PVA film can be extended by the blend of plasticizers to produce a more enveloping, more voluminous mass separating the pesticidal agent(s) from the seed surface without introducing tack or excessively degrading the film's other physical properties.

In formulations of the present invention, liquid plasticizers function as humectants. Normally, they are water-miscible and function as a slower evaporating component of the water-polyol liquid vehicle in the formulations, slowing the drying rate on application. The hygroscopic nature of these materials when combined with water also reduces the rate of water loss, which further reduces the drying rate. Therefore, the plasticizer may be used to control the drying rate of the formulation.

Liquid plasticizers that can be used in accordance with this invention are generally low molecular weight alkyl glycols or polyols (diols or triols), wherein the alkyl group is from 2 to 6 carbons in length. Specific examples include but are not limited to polyethylene glycol (e.g., ethylene glycol, diethylene glycol, triethylene glycol), propylene glycol, dipropylene glycol, butanediol, hexylene glycol, glycerol, and the like. Presently preferred glycols are propylene glycol, glycerol, dipropylene glycol, and trimethylene glycol.

In formulations of the present invention, solid plasticizers are normally water-miscible. Furthermore, solid plasticizers can be chosen to blush in the coating to reduce the dry-tack of the final film. If a solid plasticizer micro-crystallizes within the film, micro fractures can be introduced into the film to increase its moisture permeability. Reduction or retardation of germination by the formulation is thereby avoided.

Solid plasticizers that can be used in accordance with this invention are generally polyols, ureas, low molecular weight mono- and di-carboxylic acids, and their salts. Generally, suitable solid plasticizers have a melting point above 50° C. and are soluble in water to at least about 9% at 0° C. In a preferred embodiment, solid plasticizers are soluble in water to at least about 15% at 0° C. Specific examples of suitable solid plasticizers include but are not limited to sorbitol, mannitol, xylitol, trimethylol propane, saccharides, (e.g., glucose, sucrose, fructose, maltose, methyl glucoside, maltodextrin), urea, citric acid, tartaric acid, glycolic acid, and the like. Presently preferred solid plasticizers are sorbitol, trimethylol propane, glucose, methyl glucoside and urea.

In a preferred embodiment, the ratio of the liquid plasticizer to the solid plasticizer is from about 3-to-1 to about 1-to-3 parts by weight. Further, the total amount of plasticizer and the ratio of the liquid plasticizer to the solid plasticizer may be used to control the drying rate of formulations, their moisture sensitivity, and tack of the deposited film.

Polymer Emulsions

When adhesion requirements are high or when high coverage is desired, polymer emulsions (or latexes) based on polyvinyl acetate and/or ethylene vinyl acetate copolymers may be added to improve adhesion and seed appearance.

An advantage of formulations of this invention is that they are "all-inclusive", i.e. they allow for adding the polymer emulsions at the point of manufacture of the formulations, as opposed to adding them at the application site. Thus, package stability is not sacrificed and moisture uptake of seeds is not adversely affected.

Polymer emulsions that may be used in formulations of this invention are stabilized by PVA and thus, are PVA-compatible. The polymer emulsions may be added to formulations without causing "dispersant shock" that can result in an undesirable increase in viscosity or gelling. Further, since the stabilizing agents for formulation suspensions and polymer emulsions or latexes are similar, no dispersant is stripped off the latex particle or the pesticidal agent particle when they are mixed together. As a result, a stable, low viscosity mixture is obtained. This mixture is able to deposit the pesticidal agents and the polymers on seeds without the need for additional components.

Additionally, polymer emulsions may be useful to prevent the formation of an undesirable moisture barrier surrounding the seeds. Normally, films of latex dispersions containing sufficient amounts of PVA are re-dispersible in water. However, when LMW surfactants are present in seed treatment formulations, their micelles adsorb PVA, depleting the amount of PVA available to envelop the latex, polymer emulsion, or pesticidal agent particles. Thus, a permanent non-redispersible film may be formed which serves as a moisture barrier. A PVA-graft polymer combination forms a protective layer around the latex particles. This protective layer can then form a membrane that inhibits formation of this film or, alternatively, makes it re-dispersible. Thus, a permanent moisture barrier is not formed. Therefore, formulations of this invention may negate or mitigate the adverse effects of LMW surfactants on dispersion stability and seed germination that can be seen in the prior art formulations.

Specific examples of polymer emulsions usable in this invention include but are not limited to vinyl acetate homopolymer, vinyl acetate acrylic, styrene butadiene, styrene acrylic, or ethylene vinyl acetate copolymer emulsions in water, and the like. They are typically 30 to 60% solids, with a particle sizes from about 100 nm (nanometers) to about 1000 nm.

In a preferred embodiment, polymer emulsions employ PVA as the protective colloid. Polymer emulsions stabilized with protective colloids that are PVA-compatible (e.g. dextrin) are also usable. In some cases, the protective colloid is unspecified or held proprietary. These materials must be evaluated individually for stability in the formulation and safety on the seeds with germination studies.

Commercially available usable polymer emulsions include but are not limited to Atlox Semkote (Croda Uniqema.) and Airflex® 1082 (Air Products and Chemicals, Inc.).

In a preferred embodiment, "Dur-O-Set"® (Celanese Ltd.) polymer emulsions are used.

Wetting Agents and Other Additives

In one embodiment of the invention, the formulations include wetting agents. Most commercially available wetting agents are usable for the purposes of this invention.

The concentration of the wetting agents should be the minimum concentration required to achieve good wetting and film formation. When suitable wetting agents are added, the formulation should wet and form a good film. Normally, suitable wetting agents are functional at 0.1% or less by weight of the total formulation.

Examples of suitable wetting agents include but are not limited to polyaryl alkoxylated phosphate esters and their potassium salts (e.g., Soprophor® FLK (40% solids) made by Rhodia, Inc. and Stepfac® TSP PE-K (40% solids) made by Stepan Company, etc). Other suitable wetting agents include sodium dioctyl sulfosuccinates (e.g., Geropon® SDS made by Rhodia, Inc., Aerosol® OT made by Cytec Industries), and ethoxylated alcohols (e.g., Trideth-6; Rhodasurf® BC 610 made by Rhodia, Inc., Tersperse® 4894 (about 88% solids) made by Huntsman Corp.).

In another embodiment, formulations of this invention contain typical additives used in similar formulations to improve package and handling properties.

Some typical additives include:

inorganic and organic thickeners (usually added to reduce settling in the package, like Van Gel B from R.T. Vanderbilt Co.);

clays (e.g., bentonite, attapulgite);
synthetic smectites (e.g., Laponite® RD);
organic thickeners (e.g., Kelzan CC (xanthan gum) made by CP Kelco, Viscarins® (carrageenan) made by FMC Biopolymer Corp., Carbopol® polymers made by Noveon Corp., and Cellosize® (hydroxyethyl cellulose) made by Dow Chemical Company);

Slip, antiblocking agents (e.g. MPP 611XF (a micronized wax from Micro Powders Inc.) or Michem Lube 156 (a wax emulsion from Michelman Inc));

defoamers (e.g., Surfynol® 104PG (a 50% solution of tetramethyl-5-decyne-4,7-diol in propylene glycol) made by Air Products and Chemicals, Inc., Agnique DFM® 111S (silicone emulsion); and preservatives (e.g., Proxel® GXL made by Arch Chemicals, Inc. and Legend® MK made by Rohm and Haas Company).

Also, a colorant may be added to the disclosed formulations to mark the seeds as coated with pesticides.

Represenative Embodiments

All percents by weight and ratios for the components in the representative embodiments are for 100% active material, unless otherwise specified.

In a preferred embodiment, a formulation of this invention comprises: 20-to-50% by weight of the total formulation of a pesticidal agent;

1.0-to-3.0% by weight of the total formulation of a PVA-graft copolymer combination, wherein the PVA to graft copolymer ratio is from about 10-to-1 (PVA-to-graft copolymer) to about 1-to-2 (PVA-to-graft copolymer) parts by weight;

5.0-to-15% by weight of the total formulation of the blend of a liquid plasticizer and a solid plasticizer, wherein the ratio of liquid to solid plasticizer is from about 3-to-1 to about 1-to-3 parts by weight;

0-to-5.0% by weight of the total formulation of a wax slip agent or dispersion (weight percent is material "as supplied", usually about 20 to 50% solids in water);

0-to-5.0% by weight of the total formulation of a polymer emulsion (weight percent is material "as supplied", usually about 30 to 60% solids in water);

0.0-to-0.25% by weight of the total formulation of an LMW surfactant or another wetting agent;

0.1-to-1.0% by weight of the total formulation of additional formulation modifiers, such as organic and inorganic thickeners, defoamers, and antifoams; and the balance of the formulation is water to total 100% by weight.

In a more preferred embodiment, the formulation is the same as above, except that the amount of pesticidal agent is from about 35% to about 50% by weight of the total formulation; the PVA to graft copolymer ratio is from about 5-to-1 to about 1.5-to-1 parts by weight, and the amount of plasticizer is from about 7.0% to about 12.0% by weight of the total formulation.

The invention further relates to a method of applying the formulations to seeds. Techniques of seed treatment application are well known to those skilled in the art, and they may be used readily in the context of the present invention. The compositions of the present invention may be applied as a slurry or soak. Film coating and encapsulation may also be used. The coating processes are well known in the art and employ the techniques of film coating, encapsulation, immersion, etc. The method of application of the compositions of the present invention may be varied, and the invention is intended to include any technique that is to be used by one of skill in the art.

The invention further relates to a method of protecting seeds from pests comprising applying to seeds effective amounts of the formulations of the present invention.

In a preferred embodiment, the invention relates to a method of protecting seeds from pests whereby the PVA-graft copolymer combination provides a protective layer between the pesticidal agents and the seeds. In another preferred embodiment, the protective layer forms a membrane.

The phrase "effective amount" of the formulation means a sufficient amount of the formulation to provide the desired effect. In general, the formulation is employed in amounts that do not inhibit generation of the seeds and do not cause phytotoxic damage to the seeds. The amount of the formulation may vary depending on specific crops and other factors. It is well within the ordinary skill in the art to determine the necessary amount of the formulation.

The two most common application methods are slurry treatment and direct treatment. Specialized seed treatment equipment is available for each of these methods. Direct treaters meter the formulation directly onto the seed without dilution. Slurry treaters meter a water-diluted slurry made from the seed treatment formulation. The latter case will be explained in more detail to illustrate the application method.

For the slurry treatment, a known amount of formulation, containing the pesticidal agent, is diluted in water to a specific volume, and then this slurry is applied to a fixed amount of seed. The total volume of slurry (in milliliters) used per 1 Kg of seed is called the slurry rate. It is fixed and determined by the type of seed and equipment used. Table A below gives the typical slurry rates for treating the seeds of a number of crops. The amount (grams) of pesticidal agent needed on 1 Kg of seed is called the application rate. This application rate is determined experimentally, and is the amount of pesticidal agent needed to control the problem pest. For seed treatments, this application rate can range from 0.001 gram active ingredient (a.i.) per 1 Kg of seed to 5 g a.i./1 Kg of seed, depending on the inherent pesticidal effectiveness of the active ingredient. Given a target application rate, one can calculate the volume of formulation needed to deliver the desired application rate by using the formulation's loading, that is, by dividing the application rate by the grams of pesticidal agent in a liter of formulation. This volume of "formulation needed" is then subtracted from the total slurry rate to determine the amount of water needed for dilution. The slurry mixture, also called the application mixture, is then simply the volume of "formulation needed" for 1 Kg of seed diluted with water to give the total volume of slurry needed for 1 Kg of seed, the slurry rate. The total amount of slurry made can then be scaled to the actual amount of seeds to be treated.

For example, if one wants to treat 0.5 Kg of field corn seed by applying 0.6 g a.i. per 1 Kg of seed (the application rate) and one is given a seed treatment formulation (A) that contains 48% active ingredient (a.i.) with a formulation density of 1.25 grams/mL, the slurry treatment proceeds as follows. From Table A, one finds that a slurry rate of 9.4 milliliters per 1 Kg of seed should be used. From the properties of formulation (A), one calculates the loading to be 600 g a.i. per Liter (=0.48*1,250 g/L=600 g a.i./L). To deliver 0.6 g a.i. per 1 Kg of seed, one will need 0.001 L or 1 ml of formulation (=0.6 g a.i./600 g a.i./L) per 1 Kg of seed. The application mixture (slurry mixture) for 1 KG of seed is simply 1 ml of formulation (A) diluted with 8.4 ml of water (1 ml+8.4 ml=9.4 ml). To treat 0.5 kg of seed one would apply 4.7 ml (=9.4 ml/Kg of seed*0.5 Kg of seed) of the application mixture.

For small applications, a Hege 11 (Manufactured by Wintersteiger Inc of Salt Lake City Utah) seed treater can be used. This treater was used for all treatments cited in this invention. In this equipment, the seeds (0.5 Kg in field corn example above) are placed in a bowl that is equipped with a rotating disk at the bottom. The unit is started and the seeds flow in a circular motion around the sides of the bowl, driven by the rotating disk. The treater is also equipped with a smaller centrifugal disk located within the bowl, above the bottom disk, and in the plane of the seed flow. The application mixture (4.7 ml from example above) is pipetted onto the disk, which sprays the application mixture outward to coat the seeds swirling about the bowl. After 30 to 40 seconds, the unit is stopped and emptied. The seeds have now been treated with 0.6 g a.i. per Kg and are ready for planting. Commercial equipment can vary in the design of the metering method, but the basic operating principle is the same. A fixed volume of application mixture is metered onto a given weight of seed.

TABLE A

Slurry Rates

| Crop | Slurry Rate (fl.oz./cwt. Seed) | Slurry Rate (mls./KG seed) |
| --- | --- | --- |
| Sweet Corn | 19.4 | 12.6 |
| Field Corn | 14.4 | 9.4 |
| Sorghum | 14.2 | 9.2 |
| Soybeans | 8 | 5.2 |
| Cotton | 27 | 17.6 |
| Beans | 7.1 | 4.6 |
| Peas | 8.5 | 5.5 |
| Lentil | 8.5 | 5.5 |
| Rice | 32 | 20.8 |
| Barley | 10.8 | 7 |
| Wheat | 16 | 10.4 |
| Alfalfa | 19.6 | 12.6 |
| Sunflower | 16 | 10.4 |
| Peanut | 12 | 7.8 |
| Sugar Beet | 72 | 46.8 |
| Chickpea | 7.1 | 4.6 |

As used herein, all numerical values relating to amounts, weight percentages and the like, are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

The following examples are intended to illustrate the present invention and to teach one of ordinary skill in the art how to make and use the invention. They are not intended to be limiting in any way.

EXAMPLES

Example 1

Preparation of an Aqueous Seed Treatment Formulation

The amounts and the % composition of the formulation ingredients are listed in Table 1.
Liquid Vehicle Preparation
Water 1 is added to a one liter stainless steel beaker, with stirring. While stirring, Laponite® RD is dusted into the vortex. The mixture is stirred for about 30 minutes or until the solution appears clear. Then, Celvol® 24-203 (a 24% PVA solids solution), propylene glycol, sorbitol (70% solution from Archer Daniels Midland Company) are added. The mixture is stirred for about 10 minutes. Then, Tersperse® 2500, Tersperse® 4894, and Surfynol® 104PG (50% solution of Surfynol® 104 in propylene glycol from Air Products and Chemicals, Inc.) are added. The mixture is stirred for about 20 minutes. All mixing is done at room temperature.
Mill Base Preparation
Clothianidin Technical (98.2% purity, supplied by Sumitomo Chemical Company, Ltd.) is added to the liquid vehicle, with stirring. After the addition is complete, the mixture is stirred for about 20 minutes to "wet-out" clothianidin particles. The resulting crude dispersion is then placed in a basket mill (Dispermat® AE-C equipped with TML-1 basket milling system). Zirconium oxide beads of about 1.2 mm-1.7 mm size are used as the grinding media. The mixture is milled for about 3 hours at 3,000-4,000 rpm. Room temperature is maintained during the milling. A median particle size between 1.0 microns to 1.5 microns, with 90% of the particle below 5 microns, is acceptable.

Finishing Formulation

The mill base is removed from the basket mill and transferred to a one liter bottle. The yield is recorded. In a separate container, 0.17 g of Kelzan® (Xanthan gum from CP Kelco) is pre-dissolved in 33.83 g of water 2. While stirring the mill base with a laboratory mixer, Kelzan solution is added to the vortex in an amount adjusted proportionally to the yield from the mill.

As a result, a 5 pounds per gallon suspension concentrate of clothianidin suitable for application to seeds is prepared. The formulation contains about 0.06% LMW surfactant (from Tersperse® 4894). The formulation also contains 0.272% graft copolymer (from Tersperse® 2500) and about 1.4% PVA (from Celvol® 24-203), a 5-to-1 ratio of PVA to graft copolymer.

Other properties of the resulting formulation are as follows: 47.4% clothianidin content; specific gravity of 1.269; pH is 6.6; viscosity is 160 cP at 50 s-1 (pumping shear) and 2500 cP at 0.5 s−1 (at rest, settling shear). Low shear viscosity depends on the amount of a thickener (i.e., Kelzan).

TABLE 1

| Ingredient | % in Formulation | Weight (grams) |
| --- | --- | --- |
| Water 1 | 27.544 | 179.04 |
| Laponite RD | 0.151 | 0.98 |
| Celvol 24-203 (24% s) | 5.814 | 37.79 |
| Propylene glycol | 4.419 | 28.72 |
| Sorbitol Soln (70%) | 7.675 | 49.89 |
| Tersperse 2500 (35% s) | 0.777 | 5.05 |
| Tersperse 4894 (88% s) | 0.070 | 0.45 |
| Surfynol 104PG | 0.065 | 0.42 |
| Kelzan CC | 0.027 | 0.17 |
| Water 2 | 5.205 | 33.83 |
| Clothianidin Techn (98.2%) | 48.253 | 313.64 |
| Total | 100.000 | 650.00 |

Example 2

Preparation of Another Seed Treatment Formulation

The amounts and the % composition of the formulation ingredients are listed in Table 2.

Liquid Vehicle Preparation and Mill Base Preparation

Same as in Example 1.

Finishing Formulation

The mill base is removed from the basket mill and transferred to a one liter bottle. The yield is recorded. To the mill base, Airflex® 1082 (a polymer emulsion, ethylene vinyl acetate copolymer, from Air Products and Chemicals, Inc.) is added at the amount in Table 2 after adjustment for the yield. The mixture is stirred for about 15 minutes. Then, a wax emulsion, Michem Lube® 156 Kosher (a carnauba wax emulsion from Michelman Inc.), is added at the amount in Table 2 after adjustment for the yield. The mixture is stirred for about 15 minutes. In a separate container, 0.17 g of Kelzan® (Xanthan gum from CP Kelco) is pre-dissolved in water 2. While stirring the mill base with a laboratory mixer, Kelzan solution is added to the vortex in an amount adjusted proportionally to the yield from the mill.

As a result, a 5 pounds per gallon suspension concentrate of clothianidin suitable for application to seeds is prepared. The formulation contains about 0.06% LMW surfactant (from Tersperse® 4894). The formulation also contains 0.272% graft copolymer (from Tersperse® 2500) and about 1.4% PVA (from Celvol® 24-203), a 5-to-1 ratio of PVA to graft copolymer.

Some properties of the resulting formulation are as follows: 47.4% clothianidin content; specific gravity is 1.269; pH is 6.7; viscosity is 193 cP at 50 s-1 (pumping shear) and 6200 cps at 0.5 s−1 (at rest, settling shear).

TABLE 2

| Ingredient | % in Formulation | Weight (grams) |
| --- | --- | --- |
| Water 1 | 27.546 | 179.05 |
| Laponite RD | 0.151 | 0.98 |
| Celvol 24-203 (24% s) | 5.814 | 37.79 |
| Propylene glycol | 4.419 | 28.72 |
| Sorbitol Soln (70%) | 7.675 | 49.89 |
| Tersperse 2500 (35% s) | 0.777 | 5.05 |
| Tersperse 4894 (88% s) | 0.070 | 0.45 |
| Surfynol 104PG | 0.065 | 0.42 |
| Kelzan CC | 0.027 | 0.17 |
| Airflex 1082 | 2.843 | 18.48 |
| Water 2 | 1.034 | 6.72 |
| Michem Lube 156 Kosher | 1.327 | 8.62 |
| Clothianidin Techn (98.2%) | 48.253 | 313.64 |
| Total | 100.000 | 650.00 |

Example 3

Preparation of Another Seed Treatment Formulation

The amounts and the % composition of the formulation ingredients are listed in Table 3.

Liquid Vehicle Preparation

Water 1 is added to a one liter stainless steel beaker, with stirring. While stirring, Laponite® RD is dusted into the vortex. The mixture is stirred for about 30 minutes or until the solution appears clear. Then, Celvol® 24-203 (a 24% PVA solids solution), propylene glycol, sorbitol (70% solution from Archer Daniels Midland Company) are added. The mixture is stirred for about 10 minutes. Then, Tersperse® 2500, Stepfac TSP PE-K, and Surfynol® 104PG (50% solution of Surfynol® 104 in propylene glycol from Air Products and Chemicals, Inc.) are added. The mixture is stirred for about 20 minutes at room temperature (23° C.).

Mill Base Preparation

Clothianidin Technical (98.2% purity, supplied by Sumitomo Chemical Company, Ltd.) is added to the liquid vehicle, with stirring. After the addition is complete, the mixture is stirred for about 20 minutes to "wet-out" clothianidin particles. The resulting crude dispersion is then placed in the input funnel of a horizontal bead mill (Eiger Laboratory Mini Mill, Model M250). High wear resistant zirconium silica beads of about 0.8 mm size are used as the grinding media. The mixture is milled for about 11 minutes at 3,500 rpm. Room temperature is maintained during the milling. A median particle size of 1.0 micron, with 90% of the particle below 4 microns, is acceptable.

Finishing Formulation

The mill base is removed from the mill and transferred to a one liter bottle. The yield is recorded. To the mill base, Dur-O-Set Elite Ultra (25135A) (a polymer emulsion, ethylene vinyl acetate copolymer, from Celanese) is added at the amount in Table 3 after adjustment for the yield. The mixture is stirred for about 15 minutes. Then, micronized polyethylene wax, MPP 611XF (a wax from Micro Powders Inc.) is added at the amount in Table 3 after adjustment for the yield. The mixture is stirred at high sheer for about 15 minutes. In a separate container, 0.22 g of Kelzan® (Xanthan gum from CP Kelco) is pre-dissolved in water 2 using a Waring blender. While stirring the mill base with a laboratory mixer, Kelzan solution is added to the vortex in an amount adjusted proportionally to the yield from the mill.

As a result, a 5 pounds per gallon suspension concentrate of clothianidin suitable for application to seeds is prepared. The formulation contains about 0.098% LMW surfactant (from Stepfac® TSP PE-K). The formulation also contains 0.411% graft copolymer (from Tersperse® 2500) and about 1.36% PVA (from Celvol® 24-203), a 3.3-to-1 ratio of PVA to graft copolymer.

Some properties of the resulting formulation are as follows: 48.0% clothianidin content; specific gravity is 1.248; pH is 5.7; viscosity is 187 cP at 50 s-1 (pumping shear) and 8590 cps at 0.3 s-1 (at rest, settling shear).

TABLE 3

| Ingredient | % in Formulation | Weight (grams) |
|---|---|---|
| Water 1 | 28.892 | 187.80 |
| Laponite RD | 0.151 | 0.98 |
| Celvol 24-203 (24% s) | 5.655 | 36.76 |
| Propylene glycol | 4.298 | 27.94 |
| Sorbitol Soln (70%) | 6.140 | 39.91 |
| Tersperse 2500 (35% s) | 1.174 | 7.63 |
| Stepfac TSP PE-K (40% s) | 0.244 | 1.59 |
| Surfynol 104PG | 0.063 | 0.41 |
| Kelzan CC | 0.034 | 0.22 |
| Dur-O-Set Elite Ultra (25135A) | 2.824 | 18.36 |
| Water 2 | 1.344 | 8.74 |
| MPP 611XF | 0.301 | 1.96 |
| Clothianidin Techn (98.2%) | 48.880 | 317.72 |
| Total | 100.000 | 650.00 |

Example 4

Preparation of Another Seed Treatment Formulation

The amounts and the % composition of the formulation ingredients are listed in Table 4.

Van Gel B Premix4

The Van Gel B® Granules (from RT Vanderbilt Co.), 2.28 grams, are added to 54.72 g of water. The mixture is stirred at 800 rpms for 2 hours at room temperature to hydrate the clay. The 4% premix is used below as indicated.

Liquid Vehicle Preparation

The weights are given in Table 4, Column B. Water is added to a one liter stainless steel beaker, with stirring. While stirring, the Van Gel B Premix4, Celvol® 24-203 (a 24% PVA solids solution), propylene glycol, sorbitol (70% solution from Archer Daniels Midland Company), Tersperse® 2500, Stepfac® TSP PE-K, and Surfynol® 104PG (50% solution of Surfynol® 104 in propylene glycol from Air Products and Chemicals, Inc.) are added. The mixture is stirred for about 20 minutes at room temperature (23° C.).

Mill Base Preparation

Clothianidin Technical (98.1% purity, supplied by Sumitomo Chemical Company, Ltd.) is added (Table 6, Column B) to the liquid vehicle, with stirring. After the addition is complete, the mixture is stirred for about 20 minutes at high speed to "wet-out" clothianidin particles. The resulting crude dispersion is then placed in a basket mill (Dispermat® AE-C equipped with TML-1 basket milling system). Zirconium oxide beads of about 1.2 mm-1.7 mm size are used as the grinding media. The mixture is milled for about 2 hours at 3,000-3,500 rpms, and room temperature is maintained during the milling. A median particle size of 1.0 microns, with 90% of the particle below 4 microns, was obtained.

EP Diluent Preparation

The weights are given in Table 4, Column D. Water is added to a one-liter stainless steel beaker. While stirring, the Van Gel Premix4, propylene glycol, sorbitol (70% solution from Archer Daniels Midland Company), Legend® MK, and the Surfynol® 104PG (50% solution of Surfynol® 104 in propylene glycol from Air Products and Chemicals, Inc.) are added. The mixture is placed under the Dispermat® AE-C equipped with a small dissolver blade. The rpms are increased until a vortex forms in the mixture, then the Kelzan CC is dusted into the mixture. Mix at 2000 rpms for 50 minutes to dissolve the Kelzan CC. The "EP Diluent" is now ready for use.

Final Formulation

In a two-liter beaker, while mixing, the 545.71 grains of "Mill Base" are diluted with 570.29 grams of "EP Diluent". The mixture is stirred for 1 hour to complete the formulation. A 2.13 pounds (a.i.) per gallon suspension concentrate of clothianidin suitable for seed application is obtained. The formulation contains about 0.15% LMW surfactant (from Stepfac® TSP PE-K). The formulation also contains 0.364% graft copolymer (from Tersperse® 2500) and about 0.245% PVA (from Celvol® 24-203), a 1-to-1.5 ratio of PVA to graft copolymer.

TABLE 4

| | Column | | | | | |
|---|---|---|---|---|---|---|
| | A | | C | | A + C | B + D |
| | % by wt in Formulation from Mill | B Weight in Mill | % by wt in Formulation from EP | D Weight in EP | % by wt in Final | Weight (g) in Final |
| Ingredient | Base | Base (g) | Diluent | Diluent (g) | Formulation | Formulation |
| Water | 19.196 | 214.22 | 43.422 | 484.58 | 62.617 | 698.81 |
| Van Gel B Premix4 | 1.719 | 19.19 | 3.301 | 36.84 | 5.020 | 56.02 |
| Celvol 24-203 (24% s) | 1.019 | 11.37 | 0.000 | 0.00 | 1.019 | 11.37 |
| Propylene glycol | 1.044 | 11.65 | 2.005 | 22.37 | 3.049 | 34.03 |
| Sorbitol Soln (70%) | 1.044 | 11.65 | 2.005 | 22.37 | 3.049 | 34.03 |

TABLE 4-continued

| Ingredient | Column | | | | | |
|---|---|---|---|---|---|---|
| | A<br>% by wt in<br>Formulation<br>from Mill<br>Base | B<br>Weight in Mill<br>Base (g) | C<br>% by wt in<br>Formulation<br>from EP<br>Diluent | D<br>Weight in EP<br>Diluent (g) | A + C<br>% by wt in<br>Final<br>Formulation | B + D<br>Weight (g) in<br>Final<br>Formulation |
| Tersperse 2500 (35% s) | 1.041 | 11.62 | 0.000 | 0.00 | 1.041 | 11.62 |
| Stepfac TSP PE-K (40% s) | 0.372 | 4.15 | 0.000 | 0.00 | 0.372 | 4.15 |
| Surfynol 104PG | 0.036 | 0.40 | 0.068 | 0.76 | 0.104 | 1.16 |
| Kelzan CC | 0.000 | 0.00 | 0.298 | 3.33 | 0.298 | 3.33 |
| Legend MK | 0.000 | 0.00 | 0.002 | 0.03 | 0.002 | 0.03 |
| Clothianidin Techn (98.1%) | 23.427 | 261.45 | 0.000 | 0.00 | 23.427 | 261.45 |
| Total | 48.899 | 545.71 | 51.101 | 570.29 | 100.000 | 1116.00 |

Example 5

Example 5 is the same as Example 3, except that the post milling additions of a polymer emulsion and slip agent, Dur-O-Set Elite Ultra and MPP 611XF respectively, are not made. They are replaced by water. The Kelzan CC amount is also increased from 0.034% to 0.045% to maintain the viscosity.

Example 6

Preparation of Another Seed Treatment Formulation

The amounts and the % composition of the formulation ingredients are listed in Table 5.

Kelzan CC 1.5% Solution

In a separate container, 0.9 g of Kelzan® CC (Xanthan gum from CP Kelco) is pre-dissolved in 59.1 g water using a Waring blender. This 1.5% solution is added in two places during the formulation preparation, first (1) to the liquid vehicle, and secondly (2) to finish the formulation after milling.

Liquid Vehicle Preparation

Water 1 is added to a one liter stainless steel beaker, with stirring. While stirring, Celvol® 24-203 (a 24% PVA solids solution), glycerol, sorbitol (70% solution from Archer Daniels Midland Company), Tersperse® 2500, Stepfac TSP PE-K, and Surfynol® 104PG (50% solution of Surfynol® 104 in propylene glycol from Air Products and Chemicals, Inc.) are added. The 1.5% Kelzan CC 1 solution (in water) and the Michem Lube® ML 156P (a carnauba wax emulsion from Michelman Inc. are then added. The mixture is stirred for about 20 minutes at room temperature (23° C.).

Mill Base Preparation

Clothianidin Technical (98.2% purity, supplied by Sumitomo Chemical Company, Ltd.) is added to the liquid vehicle, with stirring. After the addition is complete, the mixture is stirred for about 20 minutes to "wet-out" clothianidin particles. The resulting crude dispersion is then placed in the input funnel of a horizontal bead mill (Eiger Laboratory Mini Mill, Model M250). High wear resistant zirconium silica beads of about 0.8 mm size are used as the grinding media. The mixture is milled for about 11 minutes at 3,500 rpm. Room temperature is maintained during the milling. A median particle size of 1.0 micron, with 90% of the particle below 4 microns, is acceptable.

Finishing Formulation

The mill base is removed from the mill and transferred to a one liter bottle. The yield is recorded. To the mill base, Water 2, Kelzan CC 2 (1.5% soln), and Legend MK are added at the amount in Table 5 after adjustment for the yield. The mixture is stirred for about 60 minutes. As a result, a 5 pounds per gallon (a.i.) suspension concentrate of clothianidin suitable for application to seeds is prepared. Some properties of the resulting formulation are as follows: 47.8% clothianidin content; specific gravity is 1.265; pH is 6.16; viscosity is 185 cP at 50 s-1 (pumping shear). The formulation contains about 0.098% LMW surfactant (from Stepfac® TSP PE-K). The formulation also contains 0.411% graft copolymer (from Tersperse® 2500) and about 1.36% PVA (from Celvol® 24-203), a 3.3-to-1 ratio of PVA to graft copolymer.

TABLE 5

| Ingredient | % by Wt in<br>Formulation | Weight (g) |
|---|---|---|
| Water 1 | 24.148 | 304.27 |
| Kelzan CC 1 (1.5% soln) | 0.333 | 4.20 |
| ML 156P | 2.996 | 37.75 |
| Celvol 24-203 (24% s) | 5.654 | 71.24 |
| Glycerol | 4.298 | 54.15 |
| Sorbitol Soln (70%) | 6.140 | 77.37 |
| Tersperse 2500 (35% s) | 1.174 | 14.79 |
| Stepfac TSP PE-K (40% s) | 0.244 | 3.08 |
| Surfynol 104PG | 0.063 | 0.79 |
| Water 2 | 1.875 | 23.62 |
| Kelzan CC 2 (1.5% soln) | 4.349 | 54.80 |
| Legend MK | 0.050 | 0.63 |
| Clothianidin Techn (98.2% ai) | 48.677 | 613.33 |
| Total | 100.00 | 1260.0 |

Seed Safety

To determine the effect of the formulations on germination, the formulations of Example 1 and Example 2 were coated on canola seed at a rate that deposited 400 g a.i. on 100 kilograms of seed along with a fungicide commonly used commercially. The seeds were stored, periodically sampled, and a "cold test" was performed to determine rate of germination. The procedure is well known to those familiar with the art. In brief, seeds are placed in soil or paper towels lined with soil and exposed to cold (10° C.) for a specified period, during which stress from imbibition, temperature, and microorganisms occurs. Following the cold treatment, the seeds are placed under favorable growth conditions and allowed to germinate. The percent of seeds that germinate are then measured. The results for the formulations of Example 1 and 2 are given below in Table 6. Neither formulation decreases the germination rate compared to the fungicide control alone, indicating that these formulations are safe on canola seeds over the 0, 3, 6 and 12 month storage times of the study. Tables 7 and 8 demonstrate the safety of the formulations of Examples 3 and 5 on both inbred and hybrid corn seed.

TABLE 6

Canola Seed Safety Study Over Time - Cold Test Germination (%)

| Treatment | 0 Month | 3 Months | 6 Months | 12 Months |
|---|---|---|---|---|
| Fungicide CK (FC) | 85 | 86 | 90 | 95 |
| FC + Cruiser ® 5FS @ 400 | 74 | 73 | 85 | 91 |
| FC + Poncho ® 600 @ 400 | 84 | 83 | 88 | 96 |
| FC + Example 1 @ 400 | 84 | 83 | 87 | 93 |
| FC + Example 2 @ 400 | 88 | 73 | 87 | 97 |
| LSD (0.05) | 8.846 | 14.71 | 6.592 | 3.394 |

Fungicide Check (FC) = Maxim ® 4FS + Dividend 3FS + Apron ® XL @ 1.8 + 25 + 7. All application rates equal the number of gms.a.i./100 KG seed.

TABLE 7

Saturated Cold Germination Results - Corn Inbred Seed Safety Study

| Treatment | 0 Month | 3 Months | 6 Months | 12 Months |
|---|---|---|---|---|
| FC1[1] | 96 | 90 | 93 | 83 |
| FC1 + Poncho ® 1250 system[2] | 90 | 83 | 86 | 66 |
| FC1 + Example 3 @ 1.25[3] | 97 | 91 | 95 | 86 |
| FC1 + Example 5 @ 1.25 | 95 | 92 | 91 | 80 |
| FC2[4] | 96 | 92 | 94 | 80 |
| FC2 + Cruiser ® @ 1.25 | 90 | 84 | 74 | 57 |
| FC2 + Example 5 @ 1.25 | 96 | 94 | 93 | 81 |
| LSD (0.05) | 3.631 | 4.131 | 4.814 | 7.806 |

[1]FC1 = Fungicide Check 1 (Maxim ® 4FS + Trilex ® FL + Apron ® XL + Seed Colorant (2.5 + 5 + 3 gms.a.i./100 KG seed + 16 mls. colorant/100 KG seed.
[2]Poncho ® 1250 system refers to Poncho ® 600 @ 1.25 mg.a.i./kernel + Precise ™ Seed Finisher 1007 polymer @ .6 fl.oz./cwt. Seed.
[3]All Example rates were applied at 1.25 mg.a.i./kernel
[4]FC2 = Fungicide Check 2 (Maxim ® 4FS + Dynasty ® + Apron ® XL + Seed Colorant (2.5 + 1 + 3 gms.a.i./100 KG seed + 16 mls. colorant/100 KG seed.

Table 7 shows that the formulations of Examples 3 and 5 of this invention have germination rates after 3 months that are equal to or better than the fungicide controls alone, and their absolute germination rates are 10% higher than the commercial neonicotinoids formulations at the same use rates, clothianidin in Poncho® and thiamethoxam in Cruiser®. The seed safety pattern of Examples 3 and 5 provides significant protection to corn inbred seed stored over time and continues through the 6 and 12 month germination evaluations, as portrayed in Table 7. Additionally, the same treatments applied to hybrid corn seed demonstrate the same trend of the formulations of Examples 3 and 5 that provide increased seed safety over time, as shown in Table 8, at 0, 6, and 12 months.

TABLE 8

Saturated Cold Germination Results - Corn Hybrid Seed Safety Study

| Treatment | 0 Month | 6 Months | 12 Months |
|---|---|---|---|
| FC1[1] | 96 | 97 | 96 |
| FC1 + Poncho ® 1250 system[2] | 93 | 96 | 93 |
| FC1 + Example 3 @ 1.25[3] | 97 | 98 | 94 |
| FC1 + Example 5 @ 1.25 | 98 | 99 | 97 |
| FC2[4] | 97 | 99 | 94 |
| FC2 + Cruiser ® @ 1.25 | 94 | 94 | 90 |
| FC2 + Example 5 @ 1.25 | 97 | 98 | 96 |
| LSD (0.05) | 2.385 | 2.610 | 3.256 |

[1]FC1 = Fungicide Check 1 (Maxim ® 4FS + Trilex ® FL + Apron ® XL + Seed Colorant (2.5 + 5 + 3 gms.a.i./100 KG seed + 16 mls. colorant/100 KG seed.
[2]Poncho ® 1250 system refers to Poncho ® 600 @ 1.25 mg.a.i./kernel + Precise ™ Seed Finisher 1007 polymer @ .6 fl.oz./cwt. Seed.
[3]All Example rates were applied at 1.25 mg.a.i./kernel
[4]FC2 = Fungicide Check 2 (Maxim ® 4FS + Dynasty ® + Apron ® XL + Seed Colorant (2.5 + 1 + 3 gms.a.i./100 KG seed + 16 mls. colorant/100 KG seed.

TABLE 9

Seed Safety Profile in Hybrid Corn: Saturated Cold Test Results (% Germination)

| Treatment | 0 Month | 3 Months | 6 Months | 12 Months |
|---|---|---|---|---|
| FC | 85 | 81 | 67 | 84 |
| FC + Poncho ® 1250[1] | 78 | 64 | 62 | 68 |
| FC + Poncho ® 1250 system[2] | 86 | 77 | 71 | 69 |
| FC + Example 1[3] | 82 | 72 | 67 | No Seed[4] |
| FC + Example 1 + PSF 1007 | 89 | 74 | 63 | 81 |
| FC + Example 2 | 79 | 72 | 68 | 80 |
| LSD (0.05) | 9.829 | 10.390 | 7.939 | 6.550 |

[1]Poncho ® 1250 is Poncho ® 600 applied at 1.25 mg.a.i./kernel
[2]Poncho ® 1250 system refers to Poncho ® 600 @ 1.25 mg.a.i./kernel + Precise ™ Seed Finisher (PSE) 1007 polymer @ .6 fl.oz./cwt. Seed.
[3]All Example rates were applied at 1.25 mg.a.i./kernel
[4]No Seed indicates seed sample supply was depleted.

In Table 9, the formulations of Examples 1 and 2 of this invention are equivalent to or better than the commercial standard (Poncho® 1250) up to 1 year; at which point, the formulations of the Examples have germination rates about 10% higher than the commercial standard (in absolute numbers).

TABLE 10

Insect Protection to Corn Seedlings Against Southern Corn Billbug (*Sphenophorus callosus*)

| Treatment and Application Rate | Plant Count (May 09, 2007) | Plants Damaged (May 09, 2007) | Plant Count (May 14, 2007) | Plants Damaged (May 14, 2007) | Yield (Bu/A) (Sep. 05, 2007) |
|---|---|---|---|---|---|
| Untreated | 299.3 | 44.0 | 280.0 | 86.3 | 89 |
| Poncho ® 600 @ 1.25 mg.a.i./seed | 266.3 | 13.5 | 263.0 | 11.8 | 112 |
| Example 5 @ 1.25 mg.a.i./seed | 277.0 | 1.3 | 276.3 | 9.0 | 114 |
| Example 3 @ 1.25 mg.a.i./seed | 280.0 | 1.5 | 277.5 | 9.0 | 124 |
| Counter ® 15G @ 2 lbs./A | 307.0 | 18.5 | 280.0 | 42.5 | 88 |
| LSD (P = .05) | 14.94 | 22.15 | 15.32 | 26.77 | 24.6 |
| Standard Deviation | 10.16 | 15.06 | 10.42 | 18.20 | 16.7 |
| CV | 3.55 | 140.1 | 3.78 | 79.58 | 15.13 |
| Bartlett's X2 | 7.398 | 58.893 | 5.248 | 37.213 | 1.937 |
| P (Bartlett's X2) | 0.389 | 0.001* | 0.63 | 0.0018 | 0.963 |

Table 10 shows that the formulations of Examples 5 and 3 of this invention are equivalent to or better than the commercial standard (Poncho®) in providing insect protection to corn seedlings against the Southern corn billbug (*Sphenophorus callosus*) insect.

TABLE 11

Wireworm Protection to Winter Wheat Seed and Seedlings

| Treatment | Seedling Stands (Oct. 30, 2006) |
|---|---|
| Untreated Check | 13.750 |
| Gaucho ® 600 FS @ 5 gms.a.i./100 KG seed | 15.500 |
| Gaucho ® 600 FS @ 31 gms.a.i./100 KG seed | 17.250 |
| Example 1 @ 5 gms.a.i./100 KG seed | 17.000 |
| Example 1 @ 30 gms.a.i./100 KG seed | 17.250 |
| LSD (.05) | 1.3973 |

Table 11 provides evidence of the formulation of Example 1 providing insect protection to seed and seedlings when grown in fields infested with wireworms. The formulation of Example 1 tested at 5 and 30 gms.a.i./100 KG seed provided efficacy equal to or better than the commercial control neonicotinoid insecticide, Gaucho®, which contains the active ingredient, imidacloprid.

TABLE 12

Potato Seed-Piece Application: Protection Against Wingless Aphids

| Treatment and Rate | Wingless Aphids/2 plants |
|---|---|
| Untreated Check | 4.0 |
| Cruiser ® 5FS @ 0.16 fl.oz./cwt. seed | 1.0 |
| Admire ® 2E @ 0.64 fl.oz./cwt. seed | 3.0 |
| Example 4 @ .4 fl.oz./cwt. seed | 1.3 |
| Example 4 @ .6 fl.oz./cwt. seed | 0.8 |

Table 12 shows that application of the formulation of Example 4 to plant propagules such as potato seed-pieces provides long-term protection to plant parts. The formulation of Example 4 applied at comparable rates to commercial controls Cruiser® (thiomethoxam) and Admire® (imidacloprid) gave similar or better protection against wingless aphids.

Example 7

Preparation of Another Seed Treatment Formulation

The amounts and the percent composition of the formulation ingredients are listed in Table 13.

Liquid Vehicle Preparation

Water 1 is added to a 1.2 liter stainless steel beaker. While stirring, Laponite® RD is dusted into the vortex. The mixture is stirred for about 30 minutes or until the solution clears. Celvol® 24-203 (a 24% PVA solids solution), propylene glycol, sorbitol (70% solution from Archer Daniels Midland Company), Atlox® 4913, Rhodasurf®BC 610, and Surfynol® 104PG (50% solution of Surfynol® 104 in propylene glycol from Air Products and Chemicals, Inc.) are added. The mixture is stirred for about 20 minutes at room temperature.

Mill Base Preparation

Clothianidin technical is added to the liquid vehicle while stirring. The mixture is stirred for about 20 minutes. The crude dispersion is then placed in a basket mill (Dispermat® AE-C equipped with TML-1 basket milling system). Zirconium oxide beads of about 1.2 mm-1.7 mm size are used as the grinding media. The mixture is milled for about 2 hours at 3,500 rpm. Room temperature is maintained during the milling. The milling is completed when a median particle size of 1.4 microns, with 90% of the particle below 5 microns, is achieved.

Finishing Formulation

The mill base is removed from the mill and transferred to a 1 liter jar. The yield is recorded. To the mill base, a pre-dissolved solution of Kelzan CC, Legend MK, and water 2 are added in the amounts listed in Table 13 after adjustment for the yield. The mixture is stirred for one hour. A 5 pounds (clothianidin) per gallon suspension concentrate suitable for application to seeds is obtained. The formulation contains about 0.095% wetting agent (from Rhodasurf® BC610), 0.278% graft copolymer (from Atlox® 4913), and about 1.4% PVA (from Celvol® 24-203), a 5-to-1 PVA to graft copolymer ratio.

TABLE 13

| Ingredient | % in Formulation | Weight (grams) |
|---|---|---|
| Water 1 | 28.152 | 189.16 |
| Laponite RD | 0.095 | 0.64 |
| Celvol 24-203 (24% s) | 5.935 | 39.88 |
| Propylene glycol | 4.511 | 30.31 |
| Sorbitol Soln (70%) | 7.834 | 52.64 |
| Atlox 4913 (35% s) | 0.793 | 5.33 |
| Rhodasurf BC 610 (100% s) | 0.095 | 0.64 |
| Surfynol 104PG | 0.067 | 0.45 |
| Kelzan CC | 0.027 | 0.18 |
| Legend MK | 0.000 | 0.00017 |
| Water 2 | 3.234 | 21.73 |
| Clothianidin Techn (98.2%) | 49.256 | 330.96 |
| Total | 100.000 | 671.92 |

Example 8

Preparation of Another Seed Treatment Formulation

The amounts and the percent composition of the formulation ingredients are listed in Table 14.

Liquid Vehicle Preparation

Water 1 is added to a 1.2 liter stainless steel beaker. While stirring, Laponite® RD is dusted into the vortex. The mixture is stirred for about 30 minutes or until the solution clears. A 10% solution of Celvol® V 03/240 dissolved in water is added, and stirred for 10 minutes. The propylene glycol, sorbitol (70% solution from Archer Daniels Midland Company), Terspers® 2500, Stepfac® TSP PE-K, and Surfynol® 104PG (50% solution of Surfynol® 104 in propylene glycol from Air Products and Chemicals, Inc.) are added. The mixture is stirred for about 20 minutes at room temperature.

Mill Base Preparation

Clothianidin technical is added to the liquid vehicle while stirring. The mixture is stirred for about 20 minutes. The crude dispersion is then placed in a basket mill (Dispermat® AE-C equipped with TML-1 basket milling system). Zirconium oxide beads of about 1.2 mm-1.7 mm size are used as the grinding media. The mixture is milled for about 2 hours at 3,500 rpm. Room temperature is maintained during the milling. The milling is completed when a median particle size of 1.4 microns, with 90% of the particle below 5 microns, is achieved.

Finishing Formulation

The mill base is removed from the mill and transferred to a 1 liter jar. The yield is recorded. To the mill base, a pre-dissolved solution of Kelzan CC, Legend MK, and water 2 are added in the amounts listed in Table 14 after adjustment for the yield. The mixture is stirred for one hour. A 5 pounds (clothianidin) per gallon suspension concentrate suitable for application to seeds is obtained. The formulation contains about 0.096% wetting agent (from Stepfac® TSP PE-K), 0.406% graft copolymer (from Tersperse® 2500), and about 1.36% PVA (from Celvol® V 03/240), a 3.3-to-1 PVA to graft copolymer ratio.

TABLE 14

| Ingredient | % in Formulation | Weight (grams) |
|---|---|---|
| Water 1 | 23.056 | 149.864 |
| Laponite RD | 0.150 | 0.975 |
| Celvol V 03/240 (10% s) | 13.580 | 88.27 |
| Propylene glycol | 2.120 | 13.78 |
| Sorbitol Soln (70%) | 9.090 | 59.085 |
| Tersperse 2500 (35% s) | 1.160 | 7.54 |
| Stepfac TSP PE-K (40% s) | 0.240 | 1.56 |
| Surfynol 104PG | 0.063 | 0.4095 |
| Kelzan CC | 0.033 | 0.2145 |
| Legend MK | 0.001 | 0.0065 |
| Water 2 | 2.167 | 14.0855 |
| Clothianidin Techn (98.2%) | 48.340 | 314.21 |
| Total | 100.000 | 650.00 |

Example 9

Preparation of Another Seed Treatment Formulation

The amounts and the percent composition of the formulation ingredients are listed in Table 15.

Liquid Vehicle Preparation

Water 1 is added to a 1.2 liter stainless steel beaker. While stirring, Laponite® RD is dusted into the vortex. The mixture is stirred for about 30 minutes or until the solution clears. Celvol® 09-523, propylene glycol, sorbitol (70% solution from Archer Daniels Midland Company), Tersperse® 2500, Tersperse® 4894, and Surfynol® 104PG (50% solution of Surfynol® 104 in propylene glycol from Air Products and Chemicals, Inc.) are added. The mixture is stirred for about 20 minutes at room temperature.

Mill Base Preparation

Clothianidin technical is added to the liquid vehicle while stirring. The mixture is stirred for about 20 minutes. The crude dispersion is then placed in a basket mill (Dispermat® AE-C equipped with TML-1 basket milling system). Zirconium oxide beads of about 1.2 mm-1.7 mm size are used as the grinding media. The mixture is milled for about 2 hours at 3,500 rpm. Room temperature is maintained during the milling. The milling is completed when a median particle size of 1.4 microns, with 90% of the particle below 5 microns, is achieved.

Finishing Formulation

The mill base is removed from the mill and transferred to a 1 liter jar. The yield is recorded. To the mill base, a 2.5% aqueous solution of Kelzan CC, Legend MK (added 130 ppm), Airflex 1082, and Michem Lube 156 are added in the amounts listed in Table 15 after adjustment for the yield. The mixture is stirred for one hour. A 5 pounds (clothianidin) per gallon suspension concentrate suitable for application to seeds is obtained. The formulation contains about 0.067% wetting agent (from Tersperse® 4894), 0.3% graft copolymer (from Tersperse® 2500), and about 0.6% PVA (from Celvol® 09-523), a 2-to-1 PVA to graft copolymer ratio.

TABLE 15

| Ingredient | % in Formulation | Weight (grams) |
|---|---|---|
| Water 1 | 27.66 | 190.2 |
| Laponite RD | 0.14 | 1.0 |
| Celvol 09-523 (9.5% s) | 5.81 | 40.0 |
| Propylene glycol | 4.41 | 30.3 |
| Sorbitol Soln (70%) | 7.66 | 52.6 |
| Tersperse 2500 (35% s) | 0.83 | 5.7 |
| Tersperse 4894 (88% s) | 0.08 | 0.52 |
| Surfynol 104PG | 0.07 | 0.45 |
| Kelzan CC (2.5% soln) | 1.06 | 7.3 |
| Legend MK | 0.00 | 0.0 |
| Airflex 1082 | 2.84 | 19.5 |
| Michem Lube 156 Kosher | 1.32 | 9.1 |
| Clothianidin Techn (98.2%) | 48.14 | 331.0 |
| Total | 100.000 | 687.55 |

Example 10

Preparation of Another Seed Treatment Formulation

The amounts and the percent composition of the formulation ingredients are listed in Table 16.

Liquid Vehicle Preparation

Water 1 is added to a 1.2 liter stainless steel beaker. While stirring, Van Gel ES is dusted into the vortex. The mixture is stirred for about 60 minutes to hydrate the Van Gel. Celvol® 24-203, glycerol, sorbitol (70% solution from Archer Daniels Midland Company), Tersperse® 2500, Stepfac® TSP PE-K, and Surfynol® 104PG (50% solution of Surfynol® 104 in propylene glycol from Air Products and Chemicals, Inc.) are added. The mixture is stirred for about 20 minutes at room temperature.

Mill Base Preparation

Clothianidin technical is added to the liquid vehicle while stirring. The mixture is stirred for about 20 minutes. The crude dispersion is then placed in the input funnel of a horizontal bead mill (Eiger Laboratory Mini Mill, Model M250). High wear resistant zirconium silica beads of about 0.8 mm size are used as the grinding media. The mixture is milled for about 15 minutes at 3,500 rpm. Room temperature is maintained during the milling. The milling is completed when a median particle size of 1 micron, with 90% of the particle below 4 microns, is achieved.

Finishing Formulation

The mill base is removed from the mill and transferred to a 2 liter beaker. The yield is recorded. To the mill base, a pre-dissolved solution of Kelzan CC and Legend MK in water 2 is added in the amounts listed in Table 16 after adjustment for the yield. The Michem Lube 156P is then added in the amount listed after adjusted for yield. The mixture is stirred for one hour. A 5 pounds (clothianidin) per gallon suspension concentrate suitable for application to seeds is obtained. The formulation contains about 0.098% wetting agent (from Stepfac® TSP PE-K), 0.411% graft copolymer (from Tersperse® 2500), and about 1.36% PVA (from Celvol® 24-203), a 3.3-to-1 PVA to graft copolymer ratio.

TABLE 16

| Ingredient | % in Formulation | Weight (grams) |
|---|---|---|
| Water 1 | 27.550 | 345.75 |
| Van Gel ES | 0.150 | 1.88 |
| Celvol 24-203 (24% s) | 5.655 | 70.97 |
| Glycerol | 4.298 | 53.94 |
| Sorbitol Soln (70%) | 6.140 | 77.06 |
| Tersperse 2500 (35% s) | 1.174 | 14.73 |
| Stepfac TSP PE-K (40% s) | 0.244 | 3.06 |
| Surfynol 104PG | 0.063 | 0.79 |
| Kelzan CC | 0.045 | 0.56 |
| Legend MK | 0.050 | 0.63 |
| Water 2 | 2.955 | 37.09 |
| Michem Lube 156P | 3.000 | 37.65 |
| Clothianidin Techn (98.2%) | 48.676 | 610.88 |

TABLE 17

| Ingredient | % by Weight in Formulation | Weight (g) |
|---|---|---|
| Water | 43.088 | 477.160 |
| Laponite RD | 0.149 | 1.650 |
| Celvol 24-203 (24% s) | 4.629 | 51.261 |
| Propylene glycol | 3.514 | 38.917 |
| Sorbitol Soln (70%) | 5.020 | 55.592 |
| Tersperse 2500(35% s) | 0.640 | 7.082 |
| Stepfac TSP PE-K (40% s) | 0.133 | 1.473 |
| Surfynol 104PG | 0.053 | 0.589 |
| Water | 2.247 | 24.885 |
| Kelzan CC | 0.099 | 1.095 |
| Legend MK | 0.001 | 0.014 |
| Ethaboxam Techn (98.5%) | 40.426 | 447.681 |
| Total | 100.000 | 1107.4 |

Example 11

Preparation of an Aqueous Seed Treatment Formulation

The amounts and the % composition of the formulation ingredients are listed in Table 17.

Liquid Vehicle Preparation

Water 1 is added to a one liter stainless steel beaker, with stirring. While stirring, Laponite® RD is dusted into the vortex. The mixture is stirred for about 30 minutes or until the solution appears clear. Then, Celvol® 24-203 (a 24% PVA solids solution), propylene glycol, sorbitol (70% solution from Archer Daniels Midland Company) are added. The mixture is stirred for about 10 minutes. Then, Tersperse® 2500, Stepfac TSP PE-K, and Surfynol® 104PG (50% solution of Surfynol® 104 in propylene glycol from Air Products and Chemicals, Inc.) are added. The mixture is stirred for about 20 minutes at room temperature (23° C.).

Mill Base Preparation

Ethaboxam Technical (98.5% purity, supplied by Sumitomo Chemical Company) is added to the liquid vehicle, with stirring. After the addition is complete, the mixture is stirred for about 20 minutes at high speed to "wet-out" ethaboxam particles. The resulting crude dispersion is then placed in the input funnel of a horizontal bead mill (Eiger Laboratory Mini Mill, Model M250). High wear resistant zirconium silica beads of about 0.8 mm size are used as the grinding media. The mixture is milled for about 6 minutes at 3,500 rpm. Room temperature is maintained during the milling. A median particle size of 0.8 micron, with 90% of the particle below 4 microns, is acceptable.

Finishing Formulation

The mill base is removed from the mill and transferred to a two liter beaker. The yield is recorded. In a separate container, the Kelzan® (Xanthan gum from CP Kelco) and the Legend MK are pre-dissolved in water 2 using a Waring blender to form the Kelzan solution. While stirring the mill base with a laboratory mixer, the Kelzan solution is added to the vortex in an amount adjusted proportionally to the yield from the mill.

As a result, a 3.6 pound (a.i.) per gallon suspension concentrate of ethaboxam suitable for application to seeds is prepared. The formulation contains about 0.053% LMW surfactant (from Stepfac TSP PE-K). The formulation also contains 0.224% graft copolymer (from Tersperse® 2500) and about 1.11% PVA (from Celvol 24-203), a 5.0:1 ratio of PVA to graft copolymer. Some properties of the resulting formulation are as follows: 39.8% ethaboxam content; specific gravity is 1.108; pH is 7.2; viscosity is 107 cP at 50 s-1 (pumping shear).

Example 12

Preparation of an Aqueous Seed Treatment Formulation

The amounts and the % composition of the formulation ingredients are listed in Table 18.

Liquid Vehicle Preparation

Water 1 is added to a one liter stainless steel beaker, with stirring. While stirring, Laponite® RD is dusted into the vortex. The mixture is stirred for about 30 minutes or until the solution appears clear. Then, Celvol® 24-203 (a 24% PVA solids solution), propylene glycol, sorbitol (70% solution from Archer Daniels Midland Company) are added. The mixture is stirred for about 10 minutes. Then, Tersperse® 2500, Soprophor FLK, and Surfynol® 104PG (50% solution of Surfynol® 104 in propylene glycol from Air Products and Chemicals, Inc.) are added. The mixture is stirred for about 20 minutes at room temperature (23° C.).

Mill Base Preparation

Metconazole Technical (98.7% purity, supplied by Kureha Corporation) is added to the liquid vehicle, with stirring. After the addition is complete, the mixture is stirred for about 20 minutes at high speed to "wet-out" metconazole particles. The resulting crude dispersion is then placed in a basket mill (Dispermat® AE-C equipped with TML-1 basket milling system). Zirconium oxide beads of about 1.2 mm-1.7 mm size are used as the grinding media. The mixture is milled for about 4 hours at 3,000-3,500 rpm. Room temperature is maintained during the milling. A median particle size of 1.6 microns, with 90% of the particle below 5.5 microns, was obtained.

Finishing Formulation

The mill base is removed from the mill and transferred to a two liter beaker. The yield is recorded. In a separate container, the Kelzan® (Xanthan gum from CP Kelco) and the Legend MK are added to water 2 and dissolved using a Waring blender to form the Kelzan solution. While stirring the mill base with a laboratory mixer, the Kelzan solution is added to the vortex in an amount adjusted proportionally to the yield from the mill.

As a result, a 3.6 pound (a.i.) per gallon suspension concentrate of metconazole suitable for application to seeds is prepared. The formulation contains about 0.079% LMW surfactant (from Soprophor® FLK). The formulation also contains 0.33% graft copolymer (from Tersperse® 2500) and about 1.64% PVA (from Celvol® 24-203), a 5.0:1 ratio of PVA to graft copolymer.

TABLE 18

| Ingredient | % in Formulation | Weight (g) |
| --- | --- | --- |
| Water 1 | 33.870 | 372.57 |
| Laponite RD | 0.153 | 1.69 |
| Celvol 24-203 (24% s) | 6.839 | 75.23 |
| Propylene glycol | 5.198 | 57.17 |
| Sorbitol Soln (70%) | 7.426 | 81.68 |
| Terspserse 2500 (35%) | 0.947 | 10.41 |
| Soprophor FLK (40%) | 0.197 | 2.17 |
| Surfynol 104PG (50%) | 0.077 | 0.84 |
| Water 2 | 4.707 | 51.78 |
| Kelzan CC | 0.045 | 0.49 |
| Legend MK | 0.007 | 0.08 |
| Metconazole (98.7% a.i.) | 40.528 | 445.81 |
| Total | 100.000 | 1100 |

Example 13

Preparation of Another Seed Treatment Formulation

The amounts and the % composition of the formulation ingredients are listed in Table 19.

The preparation is the same as Example 12. The weights for the components referenced in the three steps—The Liquid Vehicle Preparation, Mill Base Preparation, and Finishing Formulation—are taken from Table 19. The wetting agent is Stepfac TSP PE-K, which replaces the Soprophor FLK.

TABLE 19

| Ingredient | % in Formulation | Weight (g) |
| --- | --- | --- |
| Water 1 | 34.594 | 385.73 |
| Laponite RD | 0.150 | 1.67 |
| Celvol 24-203 (24% s) | 5.654 | 63.04 |
| Propylene glycol | 4.301 | 47.95 |
| Sorbitol Soln (70%) | 6.143 | 68.50 |
| Terspserse 2500 (35%) | 0.979 | 10.91 |
| Stepfac TSP PE-K (40%) | 0.600 | 6.68 |
| Surfynol 104PG (50%) | 0.073 | 0.82 |
| Michem Lube 156 | 2.791 | 31.12 |
| Water 2 | 4.085 | 45.55 |
| Kelzan CC | 0.100 | 1.12 |
| Legend MK | 0.004 | 0.05 |
| Metconazole (98.7% a.i.) | 40.527 | 451.89 |
| Total | 100.000 | 1115.04 |

The finished formulation from Example 13 is a 3.7 pound (a.i.) gallon, or 446 grams (active ingredient) per liter, suspension concentrate of metconazole that is suitable for application to seeds. The formulation contains 40% metconazole by weight that mills to a median particle size of 1.3 microns ($10^{-6}$ meters), and has a density of 1.11 g/cm$^3$.

The formulation contains about 0.24% LMW surfactant (from Stepfac® TSP PE-K). The formulation also contains 0.342% graft copolymer (from Terspserse® 2500) and about 1.36% PVA (from Celvol® 24-203), a 4:1 ratio of PVA to graft copolymer.

Example 14

Preparation of Another Seed Treatment Formulation

The amounts and the % composition of the formulation ingredients are listed in Table 20.

Kelzan CC 1.5% Solution

In a separate container, 1.11 g of Kelzan® CC (Xanthan gum from CP Kelco) is pre-dissolved in 72.89 g water using a Waring blender. This 1.5% solution is added in two places during the formulation preparation, first (1) to the liquid vehicle, and secondly (2) to finish the formulation after milling.

Liquid Vehicle Preparation

Water 1 is added to a one liter stainless steel beaker, with stirring. While stirring, Celvol® 24-203 (a 24% PVA solids solution), glycerol, sorbitol (70% solution from Archer Daniels Midland Company), Terspserse® 2500, Stepfac TSP PE-K, and Surfynol® 104PG (50% solution of Surfynol® 104 in propylene glycol from Air Products and Chemicals, Inc.) are added. The 1.5% Kelzan CC 1 solution (in water) and the Michem Lube® ML 156P (a carnauba wax emulsion from Michelman Inc. are then added. The mixture is stirred for about 20 minutes at room temperature (23° C.).

Mill Base Preparation

Metconazole Technical (98.7% purity, supplied by Kureha Corporation) is added to the liquid vehicle, with stirring. After the addition is complete, the mixture is stirred for about 20 minutes at high speed to "wet-out" metconazole particles. The resulting crude dispersion is then placed in a basket mill (Dispermat® AE-C equipped with TML-1 basket milling system). Zirconium oxide beads of about 1.2 mm-1.7 mm size are used as the grinding media. The mixture is milled for about 4 hours at 3,000-3,500 rpm. Room temperature is maintained during the milling. A median particle size of 1.5 microns, with 90% of the particle below 5.5 microns, was obtained.

Finishing Formulation

The mill base is removed from the mill and transferred to a two liter beaker. The yield is recorded. To the mill base, Water 2, Kelzan CC 2 (1.5% soln), and Legend MK are added at the amount in Table 20 after adjustment for the yield. The mixture is stirred for about 60 minutes. A 40% Metconazole suspension concentrate is obtained that is suitable for application to seeds. The formulation contains about 0.21% LMW surfactant (from Stepfac® TSP PE-K). The formulation also contains 0.35% graft copolymer (from Terspserse® 2500) and about 1.36% PVA (from Celvol® 24-203), a 3.9:1 ratio of PVA to graft copolymer.

TABLE 20

| Ingredient | % by Wt in Formulation | Weight (g) |
| --- | --- | --- |
| Water 1 | 31.660 | 351.93 |
| Kelzan CC 1 (1.5% soln) | 0.331 | 3.68 |
| ML 156P | 2.803 | 31.16 |
| Celvol 24-203 (24% s) | 5.650 | 62.84 |
| Glycerol | 4.300 | 47.80 |
| Sorbitol Soln (70%) | 6.140 | 68.28 |
| Terspserse 2500 (35% s) | 1.003 | 11.14 |
| Stepfac TSP PE-K (40% s) | 0.525 | 5.83 |
| Surfynol 104PG | 0.073 | 0.82 |
| Water 2 | 0.605 | 6.72 |
| Kelzan CC 2 (1.5% soln) | 6.330 | 70.31 |
| Legend MK | 0.050 | 0.56 |
| Metconazole Techn (98.7% ai) | 40.530 | 450.44 |
| Total | 100.00 | 1111.5 |

Example 15

Preparation of a Seed Treatment Formulation Containing Both Insecticide and Fungicide The amounts and the % composition of the formulation ingredients are listed in Table 21.

Kelzan CC 2.7% Solution

In a separate container, 2.7 g of Kelzan® CC (Xanthan gum from CP Kelco) is pre-dissolved in 97.3 g water using a Waring blender. This 2.7% solution is added in two places during the formulation preparation, first (1) to the liquid vehicle, and secondly (2) to finish the formulation after milling.

Liquid Vehicle Preparation

Water 1 is added to a two liter stainless steel beaker, with stirring. While stirring, Celvol® 24-203 (a 24% PVA solids solution), propylene glycol, sorbitol (70% solution from Archer Daniels Midland Company), Tersperse® 2500, Tersperse® 4894, and Surfynol® 104PG (50% solution of Surfynol® 104 in propylene glycol from Air Products and Chemicals, Inc.) are added. The 2.7% Kelzan CC 1 solution (in water) and the Michem Lube® ML 156P (a carnauba wax emulsion from Michelman Inc.) are then added. The mixture is stirred for about 20 minutes at room temperature (23° C.).

Mill Base Preparation

Clothianidin Technical (98.8% purity, supplied by Sumitomo Chemical Company) and Flutolanil Technical (98.7% purity, supplied by Gowan Company of Yuma, Ariz. USA) are added to the liquid vehicle, with stirring. After the addition is complete, the mixture is stirred for about 20 minutes at high speed to "wet-out" the particles of technical. The resulting crude dispersion is then placed in a basket mill (Dispermat® AE-C equipped with TML-1 basket milling system). Zirconium oxide beads of about 1.2 mm-1.7 mm size are used as the grinding media. The mixture is milled for about 4 hours at 3,000-3,500 rpm. Room temperature is maintained during the milling. A median particle size of 1.74 microns, with 90% of the particle below 5.0 microns, was obtained.

Finishing Formulation

The mill base is removed from the mill and transferred to a 2 liter beaker. The yield is recorded. To the mill base, Water 2, Kelzan CC 2 (2.7% soln), and Legend MK are added at the amount in Table 21 after adjustment for the yield. The mixture is stirred for about 60 minutes. A 40.5% suspension concentrate in total technicals (24.3% clothianidin and 16.2% flutolanil) is obtained that is suitable for application to seeds. The formulation contains about 0.21% LMW surfactant (from Tersperse® 4894). The formulation also contains 0.42% graft copolymer (from Tersperse® 2500) and about 1.37% PVA (from Celvol® 24-203), a 3.26:1 ratio of PVA to graft copolymer.

TABLE 21

| Ingredients | % by Weight in Formulation | Weight (g) |
| --- | --- | --- |
| Water 1 | 31.448 | 373.60 |
| Kelzan CC 1 (2.7% soln) | 0.185 | 2.20 |
| Michem Lube ML 156P (25% s) | 3.994 | 47.45 |
| Celvol 24-203 (24% s) | 5.70 | 67.72 |
| Propylene glycol | 4.29 | 50.97 |
| Sorbitol (70% soln) | 6.12 | 72.71 |
| Tersperse 2500 (35% s) | 1.20 | 14.26 |
| Tersperse 4894 (88% s) | 0.239 | 2.84 |
| Surfynol 104PG | 0.085 | 1.01 |
| Clothianidin (98.8% ai) | 24.63 | 292.60 |
| Flutolanil (98.7% ai) | 16.44 | 195.31 |
| Water 2 | 2.12 | 25.19 |
| Legend MK | 0.059 | 0.70 |
| Kelzan CC 2 (2.7% soln) | 3.49 | 41.46 |
| Total | 100.0 | 1,188 |

Example 16

Preparation of a Seed Treatment Formulation Containing Both an Insecticide and a Fungicide in the Form of a Suspension Concentrate Along with an Auxiliary Fungicide Dissolved in its Vehicle The amounts and the % composition of the formulation ingredients are listed in Table 22.

Kelzan CC 2.0% Solution

In a separate container, 2.0 g of Kelzan® CC (Xanthan gum from CP Kelco) is pre-dissolved in 98.0 g water using a Waring blender. This 2.0% solution is added in two places during the formulation preparation, first (1) to the liquid vehicle, and secondly (2) to finish the formulation after milling.

Liquid Vehicle Preparation

Water 1 is added to a two liter stainless steel beaker, with stirring. While stirring, Celvol® 24-203 (a 24% PVA solids solution), propylene glycol, urea, Tersperse® 2500, Tersperse® 4894, and Surfynol® 104PG (50% solution of Surfynol® 104 in propylene glycol from Air Products and Chemicals, Inc.) are added.

The Metalaxyl Technical (99% purity, supplied LG Life Sciences) is then added. While stirring, the mixture is heated to 55 C and held until the metalaxyl dissolves. The solution is then cooled to 23 C. The 2% Kelzan CC 1 solution (in water) and the Michem Lube® ML 156P (a carnauba wax emulsion from Michelman Inc.) are then added. The mixture is stirred for about 20 minutes at room temperature (23° C.).

Mill Base Preparation

Clothianidin Technical (98.8% purity, supplied by Sumitomo Chemical Company) and Metconazole Technical (98.7% purity, supplied by Kureha Corporation) are added to the liquid vehicle, with stirring. After the addition is complete, the mixture is stirred for about 20 minutes at high speed to "wet-out" the particles of technical. The resulting crude dispersion is then placed in a basket mill (Dispermat® AE-C equipped with TML-1 basket milling system). Zirconium oxide beads of about 1.2 mm-1.7 mm size are used as the grinding media. The mixture is milled for about 4 hours at 3,000-3,500 rpm. Room temperature is maintained during the milling. A median particle size of 1.38 microns, with 90% of the particle below 5.25 microns, was obtained.

Finishing Formulation

The mill base is removed from the mill and transferred to a 2 liter beaker. The yield is recorded. To the mill base, Water 2, Kelzan CC 2 (2% soln), and Legend MK are added at the amount in Table 22 after adjustment for the yield. The mixture is stirred for about 60 minutes. A 35% suspension concentrate in total technicals (34.1% clothianidin 0.21% Metconazole, and 0.68% metalaxyl) is obtained that is suitable for application to seeds. The formulation contains about 0.21% LMW surfactant (from Tersperse® 4894). The formulation also contains 0.469% graft copolymer (from Tersperse® 2500) and about 1.53% PVA (from Celvol® 24-203), a 3.27:1 ratio of PVA to graft copolymer.

TABLE 22

| Ingredients | % by Weight in Formulation | Weight (g) |
| --- | --- | --- |
| Water 1 | 36.679 | 440.15 |
| Kelzan CC 1 (2% soln) | 0.28 | 3.36 |
| Michelman ML 156P (25% s) | 4.58 | 54.96 |
| Celvol 24-203 (24% s) | 6.39 | 76.68 |

TABLE 22-continued

| Ingredients | % by Weight in Formulation | Weight (g) |
|---|---|---|
| Propylene glycol | 4.86 | 58.32 |
| Urea | 4.86 | 58.32 |
| Tersperse 2500 (35% s) | 1.34 | 16.08 |
| Tersperse 4894 (88% s) | 0.237 | 2.84 |
| Surfynol 104PG | 0.083 | 1.00 |
| Metalaxyl (99% ai) | 0.69 | 8.28 |
| Clothianidin (98.8% ai) | 34.52 | 414.24 |
| Metconazole (98.7% ai) | 0.22 | 2.64 |
| Water 2 | 0.47 | 5.64 |
| Legend MK | 0.051 | 0.612 |
| Kelzan CC 2 (2% soln) | 4.74 | 56.88 |
| Total | 100.0 | 1,200 |

The invention claimed is:

1. An aqueous pesticide formulation comprising a) at least one pesticidal agent; b) polyvinyl alcohol (PVA); c) a graft copolymer wherein the graft copolymer is an acrylic acid, methacrylic acid, acrylate, methacrylate or methyl methacrylate polymer with chains of another polymer extending from the acrylate polymer backbone; and d) a plasticizer wherein
   i. the amount of the pesticidal agent is from about 20% to about 50% by weight of the total formulation;
   ii. the total amount of the PVA and the graft copolymer is from about 1.0% to about 3.0% by weight of the total formulation;
   iii. the PVA to the graft copolymer ratio is from about 5-to-1 to about 1.5-to-1 parts by weight; and
   iv. the amount of the plasticizer is from about 5.0% to about 15.0% by weight of the total formulation.

2. The formulation of claim 1, wherein the pesticidal agent is an insecticide.

3. The formulation of claim 2, wherein the insecticide is a neonicotinoid.

4. The formulation of claim 3, wherein the neonicotinoid is clothianidin.

5. The formulation of claim 1, wherein the pesticidal agent is a fungicide.

6. The formulation of claim 5, wherein the fungicide is a triazole.

7. The formulation of claim 6, wherein the triazole is metconazole.

8. The formulation of claim 5, wherein the fungicide is ethaboxam.

9. The formulation of claim 1, wherein the plasticizer comprises a blend of a liquid plasticizer and a solid plasticizer.

10. The formulation of claim 1 further comprising a polymer emulsion.

11. The formulation of claim 10, wherein the polymer emulsion is based on an ethylene vinyl acetate copolymer.

12. The formulation of claim 1, wherein the graft copolymer is comb-branched.

13. The formulation of claim 1, wherein the formulation further comprises up to about 0.25% by weight of the total formulation of a low molecular weight surfactant.

14. The formulation of claim 1, wherein the plasticizer is water-miscible.

15. The formulation of claim 9, wherein the liquid plasticizer comprises an alkyl glycol or polyol selected from the group consisting of propylene glycol, glycerol, dipropylene glycol, diethylene glycol, and triethylene glycol.

16. The formulation of claim 9, wherein the solid plasticizer comprises a polyol selected from the group consisting of sorbitol, trimethylol propane, glucose, methyl glucoside, and urea.

17. The formulation of claim 1, wherein the plasticizer is a mixture of solid and liquid plasticizers having a ratio of from about 3-to-1 to about 1-to-3 parts by weight.

18. The formulation of claim 1, further comprising a wetting agent.

19. The formulation of claim 18, wherein the wetting agent is a low molecular weight surfactant.

20. The formulation of claim 1, further comprising one or more formulation modifiers.

21. The formulation of claim 20, wherein the formulation modifiers are selected from the group consisting of organic thickeners, inorganic thickeners, wax slip agents, defoamers, and antifoams.

22. The formulation of claim 20 wherein the formulation modifier comprises about 3% by weight of wax slip agent.

23. The formulation of claim 1, wherein the PVA has an average molecular weight from about 12,500 g/mole to about 125,000 g/mole.

24. An aqueous formulation comprising a) at least one pesticidal agent; b) polyvinyl alcohol (PVA); c) a graft copolymer wherein the graft copolymer is an acrylic acid, methacrylic acid, acrylate, methacrylate or methyl methacrylate polymer with chains of another polymer extending from the acrylate polymer backbone; and d) a plasticizer, wherein:
   i. the amount of the pesticidal agent is from about 35% to about 50% by weight of the total formulation;
   ii. the total amount of PVA and the graft copolymer is from about 1.0% to about 3.0% by weight of the total formulation;
   iii. the PVA to graft copolymer ratio is from about 5-to-1 to about 1.5-to-1 parts by weight; and
   iv. the amount of the plasticizer is from about 7.0% to about 12.0% by weight of the total formulation.

25. The formulation of claim 24 that further comprises about 3% by weight of a wax slip agent.

26. The formulation of claim 24 that further comprises about 3% by weight of a polymer emulsion.

27. A formulation comprising (as 100% active materials):
   i. about 0.07 to 0.25% by weight of the total formulation of a thickener;
   ii. about 1.1 to 1.4% by weight of the total formulation of PVA;
   iii. about 3.5 to 4.4% by weight of the total formulation of propylene glycol or glycerol;
   iv. about 3.5 to 4.4% by weight of the total formulation of sorbitol;
   v. about 0.2 to 0.4% by weight of the total formulation of a graft copolymer wherein the graft copolymer is an acrylic acid, methacrylic acid, acrylate, methacrylate or methyl methacrylate polymer with chains of another polymer extending from the acrylate polymer backbone;
   vi. about 0.1% by weight of the total formulation of a wetting agent;
   vii. about 0.03 to 0.1% by weight of the total formulation of a defoamer;

viii. about 0 to 0.1% by weight of the total formulation of a preservative;

ix. about 40.0 to 48.0% by weight of the total formulation of a pesticide; and x. the balance of the formulation is water to total 100% by weight.

28. The formulation of claim 27 that further comprises about 3% by weight of a wax slip agent.

29. The formulation of claim 27 that further comprises about 3% by weight of a polymer emulsion.

30. A method of protecting seeds from pests comprising applying to the seeds an effective amount of the formulation of claim 1.

31. The method of claim 30, wherein the PVA and the graft copolymer provides a protective layer between the pesticidal agent and the seeds, thereby prolonging shelf life.

32. The method of claim 30, wherein the plasticizer is used to control the drying rate of the formulation.

* * * * *